United States Patent
Nishioka

(10) Patent No.: US 11,416,992 B2
(45) Date of Patent: Aug. 16, 2022

(54) MEDICAL IMAGE PROCESSING APPARATUS, MEDICAL IMAGE DIAGNOSTIC APPARATUS, AND NON-TRANSITORY STORAGE MEDIUM

(71) Applicant: CANON MEDICAL SYSTEMS CORPORATION, Otawara (JP)

(72) Inventor: Takahiko Nishioka, Otawara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 386 days.

(21) Appl. No.: 16/751,305

(22) Filed: Jan. 24, 2020

(65) Prior Publication Data
US 2020/0155094 A1 May 21, 2020

Related U.S. Application Data

(63) Continuation of application No. PCT/JP2019/020113, filed on May 21, 2019.

(30) Foreign Application Priority Data

May 21, 2018 (JP) .............................. JP2018-097306
May 21, 2019 (JP) .............................. JP2019-095130

(51) Int. Cl.
*G06T 7/00* (2017.01)
*G06T 11/00* (2006.01)
(Continued)

(52) U.S. Cl.
CPC ............ *G06T 7/0014* (2013.01); *A61B 6/503* (2013.01); *G06T 11/008* (2013.01); *G06T 15/08* (2013.01);
(Continued)

(58) Field of Classification Search
CPC ..... G06T 7/0014; G06T 11/008; G06T 15/08; G06T 2207/10081; G06T 2207/30048;
(Continued)

(56) References Cited

U.S. PATENT DOCUMENTS 8,920,322 B2 * 12/2014 Mansi .................. A61B 8/5238
600/407
2010/0022823 A1 * 1/2010 Goldfarb ................ A61B 17/29
600/37

(Continued)

FOREIGN PATENT DOCUMENTS

| JP | 2015-226693 A | 12/2015 | |
|---|---|---|---|
| JP | 2017-18305 A | 1/2017 | |
| WO | WO-2019154737 A1 * | 8/2019 | ........... A61B 8/0883 |

OTHER PUBLICATIONS

Robicsek, Francis, et al. "The congenitally bicuspid aortic valve: how does it function? Why does it fail?." The Annals of thoracic surgery 77.1 (2004): 177-185.*

(Continued)

*Primary Examiner* — Shefali D Goradia
(74) *Attorney, Agent, or Firm* — Oblon, McClelland, Maier & Neustadt, L.L.P.

(57) ABSTRACT

A medical image processing apparatus of an embodiment includes a processing circuitry. The processing circuitry extracts a plurality of valve leaflets of a heart valve from image data of a subject. The processing circuitry measures, with respect to at least one valve leaflet of the valve leaflets, a length of a region at which the valve leaflet is in contact with another valve leaflet, in a predetermined reference direction. The processing circuitry controls a display to display a distribution of the length at each of a plurality of positions on the valve leaflet.

26 Claims, 16 Drawing Sheets

(51) Int. Cl.
*G06T 15/08* (2011.01)
*A61B 6/00* (2006.01)
*G16H 30/40* (2018.01)

(52) U.S. Cl.
CPC ........... *A61B 6/5217* (2013.01); *A61B 6/5223* (2013.01); *G06T 2207/10081* (2013.01); *G06T 2207/30048* (2013.01); *G06T 2207/30104* (2013.01); *G16H 30/40* (2018.01)

(58) Field of Classification Search
CPC .......... G06T 2207/30104; A61B 6/503; A61B 6/5217; A61B 6/5223; G16H 30/40
See application file for complete search history.

(56) References Cited

U.S. PATENT DOCUMENTS

| | | |
|---|---|---|
| 2010/0240996 A1 | 9/2010 | Ionasec et al. |
| 2015/0178938 A1 | 6/2015 | Gorman, III et al. |
| 2015/0348263 A1 | 12/2015 | Yamamori et al. |
| 2016/0171766 A1 | 6/2016 | Grbic et al. |
| 2017/0007201 A1 | 1/2017 | Kobayashi et al. |
| 2017/0128203 A1* | 5/2017 | Zhang .................. A61F 2/2418 |
| 2017/0301096 A1* | 10/2017 | Weese ..................... G06T 19/00 |
| 2019/0336286 A1* | 11/2019 | Chen ..................... A61F 2/2448 |
| 2019/0343633 A1* | 11/2019 | Garvin ................. A61F 2/2457 |

OTHER PUBLICATIONS

Gunning, Paul S., Ted J. Vaughan, and Laoise M. McNamara. "Simulation of self expanding transcatheter aortic valve in a realistic aortic root: implications of deployment geometry on leaflet deformation." Annals of biomedical engineering 42.9 (2014): 1989-2001.*

International Search Report dated Aug. 20, 2019 in PCT/JP2019/020113 filed May 21, 2019, 1 page.

* cited by examiner

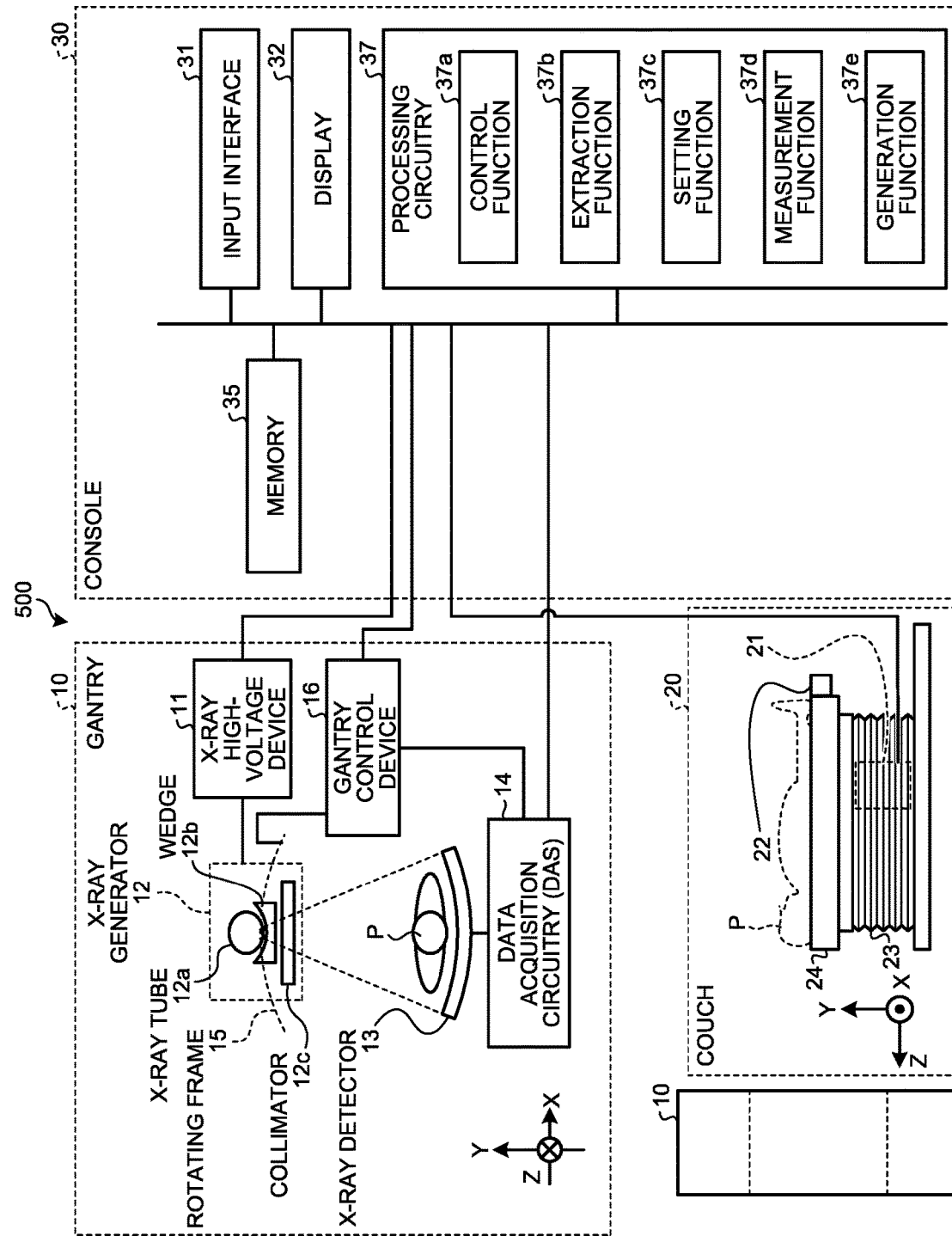

MEDICAL IMAGE PROCESSING APPARATUS, MEDICAL IMAGE DIAGNOSTIC APPARATUS, AND NON-TRANSITORY STORAGE MEDIUM

CROSS-REFERENCE TO RELATED APPLICATIONS

This application is a continuation of International Application No. PCT/JP2019/020113, filed on May 21, 2019 which claims the benefit of priority of the prior Japanese Patent Application No. 2018-097306, filed on May 21, 2018 and Japanese Patent Application No. 2019-095130, filed on May 21, 2019, the entire contents of which are incorporated herein by reference.

FIELD

Embodiments described herein relate generally to a medical image processing apparatus, a medical image diagnostic apparatus, and a non-transitory storage medium.

BACKGROUND

In the related art, in preoperative examination for various diseases (for example, aortic valve insufficiency or mitral valve insufficiency) of a valve (heart valve) such as an aortic valve and a mitral valve, a user such as a doctor confirms the backflow of blood by using an ultrasonic diagnostic apparatus, for example.

BRIEF DESCRIPTION OF THE DRAWINGS

FIG. 26 is a diagram illustrating an example of a configuration of an X-ray CT apparatus according to a third embodiment.

DETAILED DESCRIPTION

A medical image processing apparatus of an embodiment includes processing circuitry. The processing circuitry extracts a plurality of valve leaflets of a heart valve from image data of a subject. The processing circuitry measures, with respect to at least one valve leaflet of the valve leaflets, a length of a region at which the valve leaflet is in contact with another valve leaflet, in a predetermined reference direction. The processing circuitry controls a display to display a distribution of the length at each of a plurality of positions on the valve leaflet.

Hereinafter, with reference to the drawings, the medical image processing apparatus, a medical image diagnostic apparatus, and a medical image processing program will be described. Content described in one embodiment or modification example may also be applied to other embodiments or modification examples in the same manner.

First Embodiment

Figure 1:
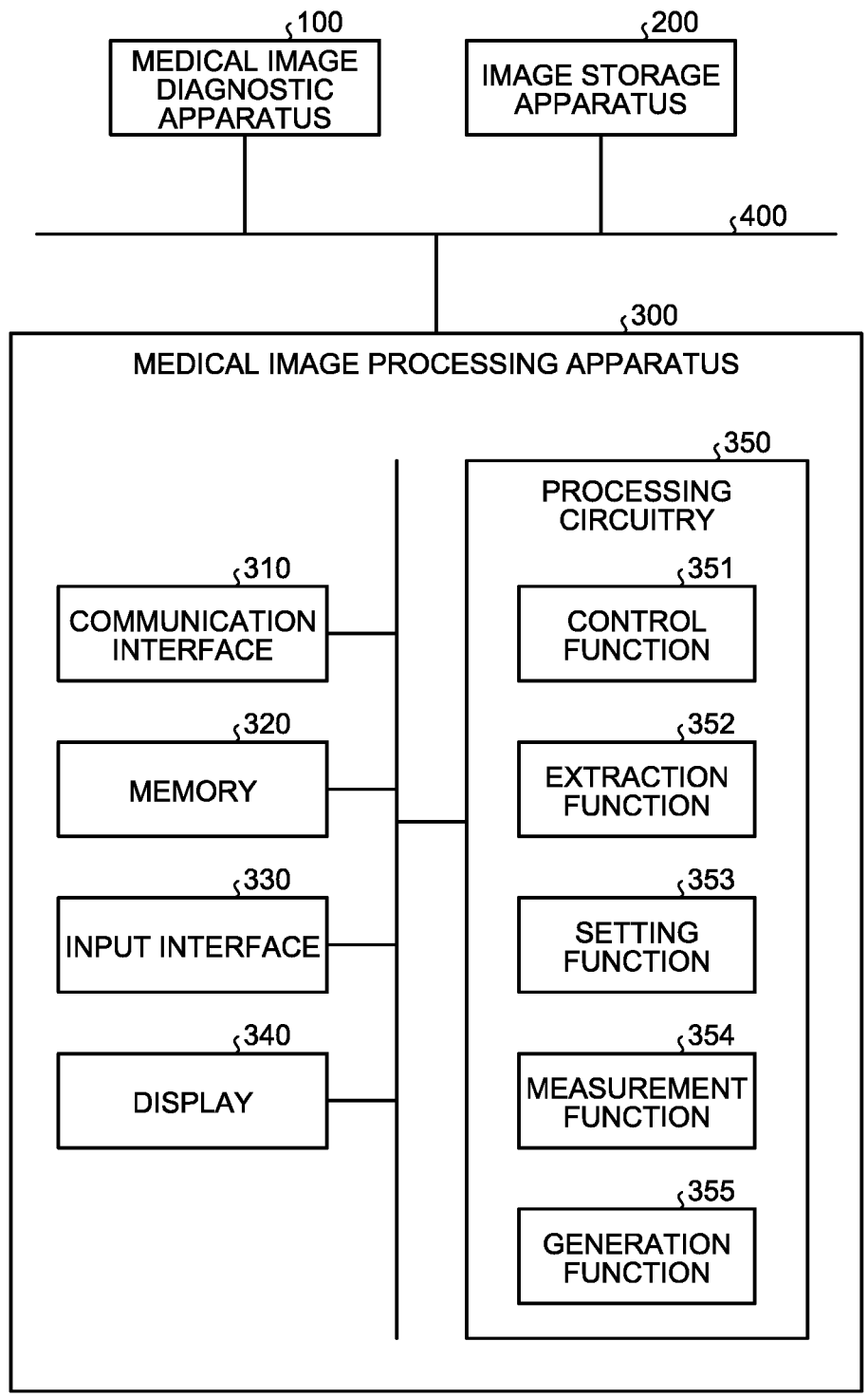
FIG. 1 is a diagram illustrating an example of a configuration of a medical image processing apparatus according to a first embodiment.

First, a first embodiment will be described. FIG. 1 is a diagram illustrating an example of a configuration of a medical image processing apparatus 300 according to the first embodiment. As illustrated in FIG. 1, the medical image processing apparatus 300 is connected to a medical image diagnostic apparatus 100 and an image storage apparatus 200 via a network 400. The configuration illustrated in FIG. 1 is merely an example, and in addition to the medical image diagnostic apparatus 100, the image storage apparatus 200, and the medical image processing apparatus 300 illustrated in FIG. 1, various apparatuses such as terminal apparatuses may also be connected to the network 400.

The medical image diagnostic apparatus 100, for example, is an X-ray CT (Computed Tomography) apparatus, an ultrasonic diagnostic apparatus, a magnetic resonance imaging (MRI) apparatus, or an X-ray diagnostic apparatus. The medical image diagnostic apparatus 100 is not limited to the aforementioned medical image diagnostic apparatus (the X-ray CT apparatus, the ultrasonic diagnostic apparatus, the magnetic resonance imaging apparatus, and the X-ray diagnostic apparatus), and may be other medical image diagnostic apparatuses. The medical image diagnostic apparatus 100 acquires three-dimensional image data including a valve of a heart (a heart valve) of a subject. The three-dimensional image data is also referred to as volume data.

When the medical image diagnostic apparatus 100 is the X-ray CT apparatus, the X-ray CT apparatus collects CT image data of the subject. For example, the X-ray CT apparatus revolves an X-ray tube and an X-ray detector approximately centered at the subject, and collects projection data by detecting X-rays transmitted through the subject. On the basis of the collected projection data, the X-ray CT apparatus generates the three-dimensional CT image data. For example, the X-ray CT apparatus collects the projection data obtained by imaging a region including the valve of the heart of the subject, and generates the three-dimensional CT image data on the basis of the collected projection data. Then, the X-ray CT apparatus transmits the generated three-dimensional CT image data to the image storage apparatus 200 and the medical image processing apparatus 300.

In addition, the X-ray CT apparatus may collect four-dimensional CT image data including the valve of the heart of the subject, and transmit the collected four-dimensional CT image data to the image storage apparatus 200 and the medical image processing apparatus 300. The four-dimensional CT image data including the valve of the heart, for example, is composed of a plurality of pieces of time-series three-dimensional CT image data. That is, the four-dimensional CT image data including the valve of the heart is composed of a plurality of pieces of three-dimensional CT image data with different imaging times (time phases). Each piece of three-dimensional CT image data constituting the four-dimensional CT image data is generated on the basis of the projection data obtained by imaging the region including the valve of the heart of the subject. The three-dimensional CT image data and the four-dimensional CT image data are examples of image data. Furthermore, there is a case where the three-dimensional CT image data and the four-dimensional CT image data are simply referred to as "CT image data".

Furthermore, the valve of the heart of the subject, for example, includes a mitral valve, an aortic valve, a tricuspid valve, or a pulmonary valve. Hereinafter, a case where the medical image diagnostic apparatus 100 is the X-ray CT apparatus will be described as an example; however, the medical image diagnostic apparatus 100 may be the ultrasonic diagnostic apparatus or the magnetic resonance imaging apparatus. That is, the medical image processing apparatus 300 may perform the same processes as various processes, which will be described below, on image data collected by the ultrasonic diagnostic apparatus or the magnetic resonance imaging apparatus.

The image storage apparatus 200 stores the CT image data collected by the medical image diagnostic apparatus 100 which is the X-ray CT apparatus. For example, the image storage apparatus 200 is implemented by a computer apparatus such as a server apparatus. The image storage apparatus 200 acquires the CT image data from the medical image diagnostic apparatus 100 via the network 400, and stores the acquired CT image data in a memory such as a hard disk and an optical disc provided inside or outside the apparatus. For example, the image storage apparatus 200 acquires the three-dimensional CT image data or the four-dimensional CT image data from the medical image diagnostic apparatus 100 which is the X-ray CT apparatus, and stores the acquired CT image data in the memory. Furthermore, the image storage apparatus 200 transmits the CT image data stored in the memory to the medical image processing apparatus 300 in response to a request from the medical image processing apparatus 300.

The medical image processing apparatus 300 acquires the CT image data from the medical image diagnostic apparatus 100 and the image storage apparatus 200 via the network 400, and processes the acquired CT image data. For example, the medical image processing apparatus 300 acquires the three-dimensional CT image data or the four-dimensional CT image data from the medical image diagnostic apparatus 100 or the image storage apparatus 200, and performs various kinds of image processing on the acquired CT image data. Then, the medical image processing apparatus 300 displays an image after the image processing (for example, an image for display) or the like on a display 340.

As illustrated in FIG. 1, the medical image processing apparatus 300 has a communication interface 310, a memory 320, an input interface 330, the display 340, and processing circuitry 350.

The communication interface 310 is connected to the processing circuitry 350 and controls transmission of various pieces of data performed between the medical image diagnostic apparatus 100 and the image storage apparatus 200 connected via the network 400 and communication performed between the medical image diagnostic apparatus 100 and the image storage apparatus 200. For example, the communication interface 310 is implemented by a network card, a network adapter, a network interface controller (NIC), or the like. For example, the communication interface 310 receives the three-dimensional CT image data or the four-dimensional CT image data from the medical image diagnostic apparatus 100 or the image storage apparatus 200, and outputs the received CT image data to the processing circuitry 350.

The memory 320 is connected to the processing circuitry 350 and stores therein various pieces of data. For example, the memory 320 is implemented by a semiconductor memory element such as a random access memory (RAM) and a flash memory, a hard disk, or an optical disc. In the present embodiment, the memory 320 stores therein the three-dimensional CT image data or the four-dimensional CT image data received from the medical image diagnostic apparatus 100 or the image storage apparatus 200.

Furthermore, the memory 320 stores therein various kinds of information to be used for the processing of the processing circuitry 350, processing results of the processing circuitry 350, or the like. For example, the memory 320 stores therein image data for display generated by the processing circuitry 350, measurement results of a measurement function 354 to be described below.

The input interface 330 is connected to the processing circuitry 350, converts an input manipulation received from an operator into an electrical signal, and outputs the electrical signal to the processing circuitry 350. In the present specification, the input interface 330 is not limited to be equipped with physical manipulation parts such as a mouse and a keyboard. For example, an electrical signal processing circuitry, which receives an electrical signal corresponding to an input manipulation from an external input device provided separately from the apparatus and outputs the electrical signal to a control circuit, is also included in an example of an input interface.

For example, the input interface 330 is implemented by a touch pad for performing an input manipulation by touching a trackball, a switch button, a mouse, a keyboard, or a manipulation surface for performing various types of setting, a touch screen in which a display screen and the touch pad are integrally formed with each other, a non-contact input interface using an optical sensor, or a voice input interface.

The display 340 is connected to the processing circuitry 350 and displays various kinds of information and various images output from the processing circuitry 350. For example, the display 340 is implemented by a liquid crystal monitor, a cathode ray tube (CRT) monitor, or a touch panel. For example, the display 340 displays a graphical user interface (GUI) for receiving an instruction of an operator, various images for display, and various processing results of the processing circuitry 350. The display 340 is an example of a display unit.

The processing circuitry 350 controls each constituent element of the medical image processing apparatus 300 in response to an input manipulation received from an operator via the input interface 330. For example, the processing circuitry 350 is implemented by a processor. In the present embodiment, the processing circuitry 350 allows the three-dimensional CT image data or the four-dimensional CT image data output from the communication interface 310 to be stored in the memory 320. Furthermore, the processing circuitry 350 reads the three-dimensional CT image data or the four-dimensional CT image data from the memory 320, and controls the display 340 to display an image for display indicated by image data for display generated from the read CT image data.

So far, the overall configuration of the medical image processing apparatus according to the present embodiment has been described. Hereinafter, a description will be given for a case where a user such as a doctor confirms the backflow of blood in the valve of the heart of the subject by the ultrasonic diagnostic apparatus in preoperative examination. In such a case, since the detailed condition of the valve is not presented to the user, the user has a difficulty in understanding the detailed condition of the valve. Therefore, for example, before an operation, the user has a difficulty in determining an operation method of the valve such as whether it is better to perform a mitral valve replacement operation or whether it is better to perform a mitral valve repair operation.

In this regard, the medical image processing apparatus 300 according to the present embodiment is configured to be able to allow the user to understand the detailed condition of the valve as will be described below.

As illustrated in FIG. 1, the processing circuitry 350 according to the first embodiment has a control function 351, an extraction function 352, a setting function 353, the measurement function 354, and a generation function 355. For example, processing functions of the control function 351, the extraction function 352, the setting function 353, the measurement function 354, and the generation function 355, which are constituent elements of the processing circuitry 350 illustrated in FIG. 1, are recorded in the memory 320 in the form of computer programs executable by a computer. The processing circuitry 350 reads the computer programs from the memory 320 and performs the functions corresponding to the computer programs by executing the read computer programs. In other words, the processing circuitry 350 having read the computer programs has the functions indicated in the processing circuitry 350 of FIG. 1.

All the processing functions of the control function 351, the extraction function 352, the setting function 353, the measurement function 354, and the generation function 355 may also be recorded in the memory 320 in the form of a single computer program executable by a computer. For example, such a computer program is also referred to as a medical image processing program. In such a case, the processing circuitry 350 reads the medical image processing program from the memory 320 and executes the read medical image processing program, thereby implementing the control function 351, the extraction function 352, the setting function 353, the measurement function 354, and the generation function 355 corresponding to the medical image processing program.

The control function 351 is an example of a display control unit. The extraction function 352 is an example of an extraction unit. The setting function 353 is an example of a setting unit. The measurement function 354 is an example of a measurement unit. The generation function 355 is an example of a generation unit.

The control function 351 performs overall control of the medical image processing apparatus 300. For example, the control function 351 acquires the CT image data from the medical image diagnostic apparatus 100 or the image storage apparatus 200 via the communication interface 310. For example, the control function 351 acquires the three-dimensional CT image data including the valve of the heart of the subject or the four-dimensional CT image data including the valve of the heart of the subject. Then, the control function 351 stores the acquired CT image data in the memory 320. Furthermore, the control function 351 controls the display 340 to display an image for display indicated by image data for display generated from the CT image data by various types of image processing. Furthermore, the control function 351 controls the display 340 to display a measurement result measured by the measurement function 354.

The extraction function 352 extracts a plurality of valve leaflets constituting the valve from the CT image data including the valve of the subject. That is, the extraction function 352 extracts the valve leaflets of the heart valve from the image data of the subject. Hereinafter, an example of various processes to be performed by the extraction function 352 will be described. For example, the extraction function 352 first acquires the three-dimensional CT image data or the four-dimensional CT image data stored in the memory 320.

Hereinafter, a case where the CT image data acquired by the extraction function 352 is the three-dimensional CT image data will be described. For example, the user sends a transmission request of three-dimensional CT image data to the medical image diagnostic apparatus 100 or the image storage apparatus 200 via the input interface 330, the three-dimensional CT image data being obtained by imaging the valve to be observed by the user at a time phase at which the user desires observation. By so doing, the medical image diagnostic apparatus 100 or the image storage apparatus 200 having received the transmission request transmits the three-dimensional CT image data satisfying the transmission request to the medical image processing apparatus 300. The transmitted three-dimensional CT image data is the three-dimensional CT image data acquired by the extraction function 352.

The valve to be observed by the user and the time phase at which the user desires observation will be described using a specific example. For example, when the subject's heart is in a normal condition, an aortic valve is closed and a mitral valve is opened during diastole, so that blood flows from the left atrium to the left ventricle. In mitral stenosis, since the opening of the mitral valve is narrowed, the amount of the blood flowing from the left atrium to the left ventricle is reduced during the diastole. Therefore, when the subject is suspected to have the mitral stenosis, the user such as a doctor desires to understand the detailed condition of the mitral valve during the diastole.

Furthermore, in aortic valve insufficiency (aortic valve regurgitation), since the aortic valve is not sufficiently closed during the diastole, a part of the blood flows back to the left ventricle. Therefore, the user desires to understand the detailed status of the aortic valve during the diastole.

Furthermore, when the subject is in a normal condition, since the mitral valve is closed and the aortic valve is opened during systole, the blood is sent from the left ventricle to the aorta. In mitral valve insufficiency (mitral valve regurgitation), when the left ventricle contracts during the systole, since the mitral valve is not sufficiently closed, a part of the blood flows back to the left atrium. Therefore, when the subject is suspected to have the mitral stenosis, the user desires to understand the detailed condition of the mitral valve during the systole.

Furthermore, in aortic stenosis, since the opening of the aortic valve is narrowed during the systole, the amount of the blood flowing from the left ventricle to the aorta is reduced during the systole. Therefore, when the subject is suspected to have the aortic stenosis, the user desires to understand the detailed condition of the aortic valve during the systole.

Next, a case where the CT image data acquired by the extraction function 352 is the four-dimensional CT image data will be described. In such a case, the extraction function 352 selects three-dimensional CT image data of one time phase designated by the user from three-dimensional CT image data of a plurality of time phases constituting the four-dimensional CT image data. Then, the extraction function 352 acquires the selected three-dimensional CT image data.

Then, the extraction function 352 extracts each of the valve leaflets constituting the valve of the heart of the subject from the acquired three-dimensional CT image data. In such a case, the extraction function 352 extracts the valve leaflets one by one from the three-dimensional CT image data by using various known technologies. For example, the memory 320 may store therein information indicating the standard shape of the valve leaflet, and the extraction function 352 may acquire the information indicating the standard shape of the valve leaflet from the memory 320. Then, the extraction function 352 may detect a portion similar to the shape indicated by the acquired information from the three-dimensional CT image data, and extract the detected portion from the three-dimensional CT image data.

Figure 2:
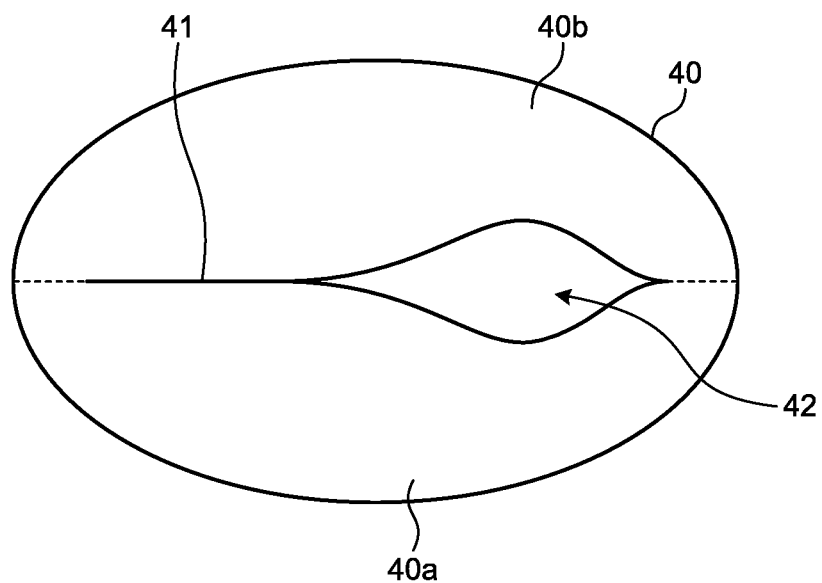
FIG. 2 is a diagram illustrating an example of a plurality of valve leaflets extracted by an extraction function according to the first embodiment.
Figure 3:
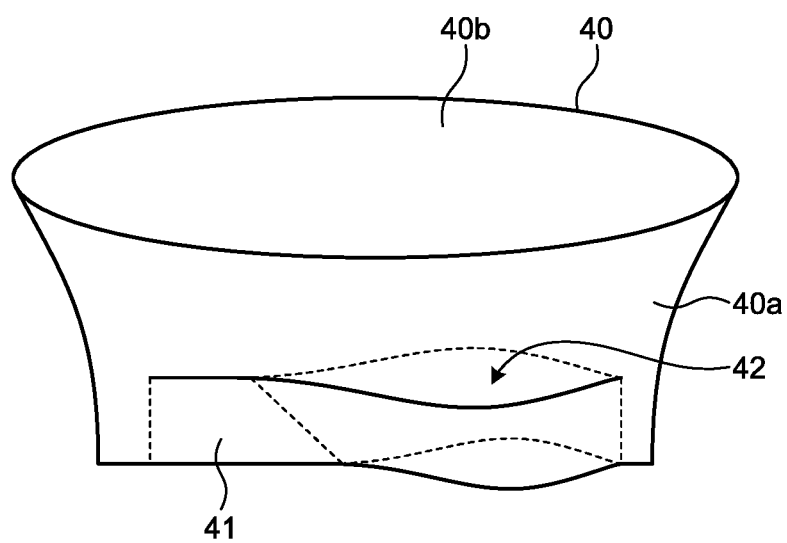
FIG. 3 is a diagram illustrating an example of the valve leaflets extracted by the extraction function according to the first embodiment.

FIG. 2 and FIG. 3 are diagrams illustrating an example of the valve leaflets extracted by the extraction function 352 according to the first embodiment. FIG. 2 is a diagram when a mitral valve 40 is viewed from an upstream side in the flow of blood passing through the mitral valve 40. FIG. 3 is a perspective view of the mitral valve 40.

As illustrated in FIG. 2 and FIG. 3, the mitral valve 40 is composed of two valve leaflet 40a and valve leaflet 40b extracted by the extraction function 352. In the example of FIG. 2 and FIG. 3, there is a region (a contact region) 41 at which the valve leaflet 40a and the valve leaflet 40b contact with each other. Since the valve leaflet 40a and the valve leaflet 40b contact with each other (are joined to each other), the contact region 41 is common to the valve leaflet 40a and the valve leaflet 40b. The contact between the valve leaflet 40a and the valve leaflet 40b also expresses that the valve leaflet 40a overlaps the valve leaflet 40b.

Furthermore, in the example of FIG. 2 and FIG. 3, since a part of the valve leaflet 40a and a part of the valve leaflet 40b are separated (spaced) from each other, there is a region (a separation region) 42 formed by a part of the valve leaflet 40a and a part of the valve leaflet 40b. That is, there is the separation region 42 which is a region between a part of the valve leaflet 40a and a part of the valve leaflet 40b separated from each other. A range of the separation region 42 in a blood flow direction, for example, is a range from an upstream end of the contact region 41 in the blood flow direction to a downstream end of the contact region 41 in the blood flow direction. The downstream end of the contact region 41 in the blood flow direction is the position of a reference surface 50 set by the setting function 353, as will be described below. Furthermore, the separation region 42, for example, may be a region smaller than a threshold value for determining that the valve leaflet 40a and the valve leaflet 40b are separated from each other.

Returning back to the description of FIG. 1, the setting function 353 sets a reference surface related to some valve leaflets of the valve leaflets extracted by the extraction function 352. Hereinafter, an example of a process of setting the reference surface by the setting function 353 will be described employing a case where an object to be processed is the mitral valve 40 as an example.

Figure 4:
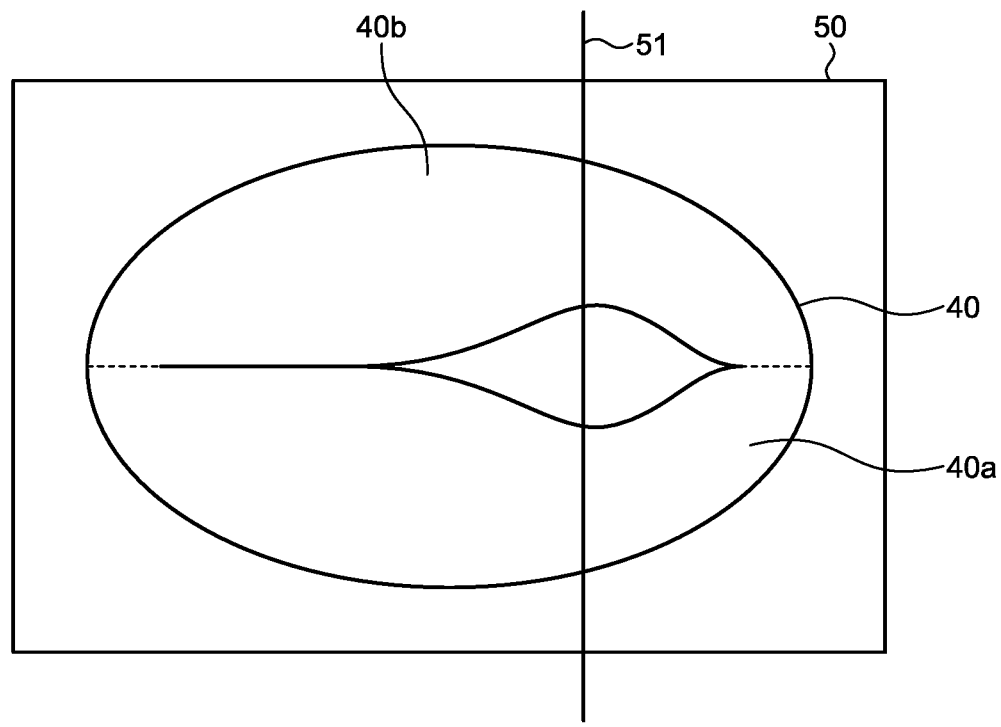
FIG. 4 is a diagram for explaining an example of a process performed by a setting function according to the first embodiment.
Figure 5:
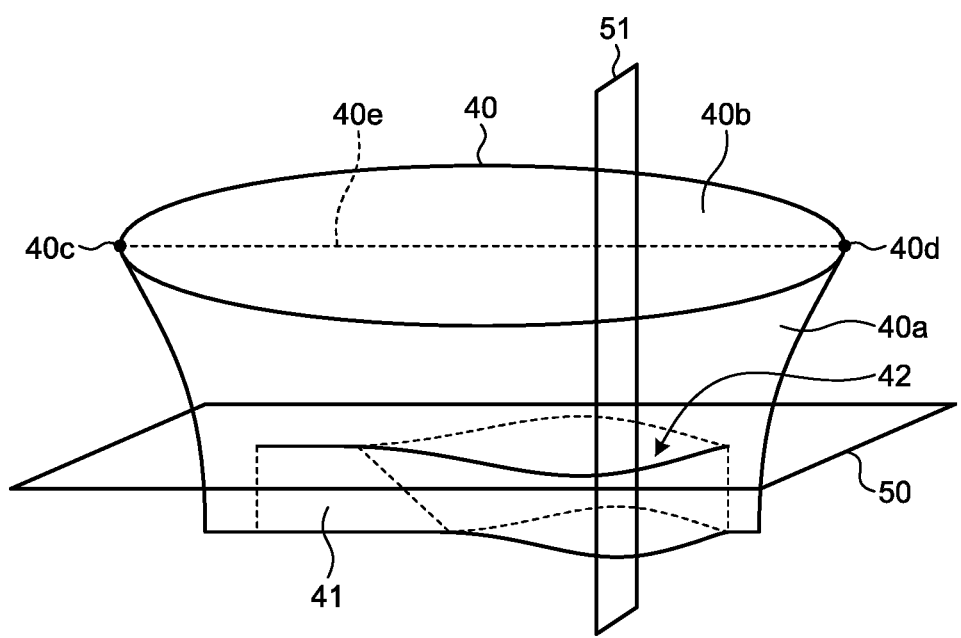
FIG. 5 is a diagram for explaining an example of a process performed by the setting function according to the first embodiment.

FIG. 4 to FIG. 7 are diagrams for explaining an example of the process performed by the setting function 353 according to the first embodiment. For example, as illustrated in FIG. 4 and FIG. 5, the setting function 353 sets the reference surface (a first reference surface) 50 related to the valve leaflets 40a and 40b.

Figure 6:
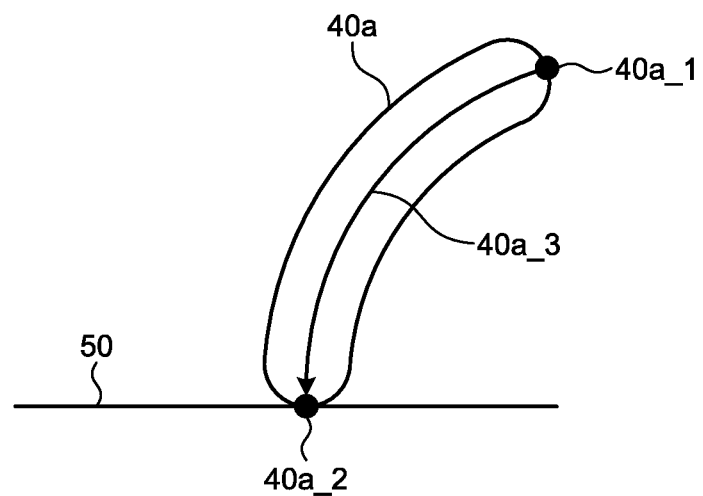
FIG. 6 is a diagram for explaining an example of a process performed by the setting function according to the first embodiment.

The setting function 353 sets the reference surface 50 to be orthogonal or approximately orthogonal to the blood flow direction. As described above, the setting function 353 sets the reference surface 50 perpendicular or approximately perpendicular to the blood flow direction. That is, the setting function 353 sets the reference surface 50 so as to intersect with the blood flow direction. FIG. 6 illustrates a direction 40a_3 from a root portion 40a_1 to a tip portion 40a_2 of one valve leaflet 40a of the two valve leaflets 40a and 40b. The direction 40a_3 is a direction toward the tip portion 40a_2 from the root portion 40a_1 along the valve leaflet 40a. The direction 40a_3 in the tip portion 40a_2 is considered to be the same direction or approximately the same direction as the blood flow direction.

As illustrated in FIG. 6, the setting function 353 sets the reference surface 50 that contacts with the tip portion 40a_2 and is orthogonal to the direction 40a_3. In this way, the reference surface 50 orthogonal or approximately orthogonal to the blood flow direction is set. The setting function 353 may also set the reference surface 50 orthogonal or approximately orthogonal to the blood flow direction by performing the same process on the valve leaflet 40b instead of the valve leaflet 40a. That is, the setting function 353 sets the reference surface 50 intersecting with the blood flow direction by performing the aforementioned process on one of the valve leaflets constituting the valve.

The reference surface 50 may have a shape following the shape of the tip portion 40a_2. In such a case, since the shape of the reference surface 50 depends on the shape of the tip portion 40a_2, a case where the reference surface 50 is a curved surface or a plane surface is considered.

The setting function 353 can move the set reference surface 50 along the normal direction of the reference surface 50 or the blood flow direction to be arranged in a predetermined arrangeable range (arrangeable range). When the reference surface 50 is moved within the arrangeable range, an MPR image corresponding to the moved position is newly generated by the generation function 355 to be described below, and the new MPR image is displayed on the display by the control function 351 to be described below. For example, a new MPR image 76 (see FIG. 13) and a new MPR image 80 (see FIG. 15) are generated by the generation function 355, and the new MPR image 76 and the new MPR image 80 are displayed by the control function 351. Since a plane passing through the starting portion of a coronary artery relatively coincides with an overlapping portion of the valve, it is considered to arrange the reference surface 50 to pass through the starting portion of the coronary artery.

The arrangeable range of the reference surface 50 is different between when the two valve leaflet 40a and valve leaflet 40b contact with each other in at least one portion and when they do not completely contact with each other.

First, the arrangeable range of the reference surface 50 when the two valve leaflet 40a and valve leaflet 40b contact with each other in at least one portion will be described. For example, the setting function 353 can move and arrange the reference surface 50 within the arrangeable range from the upstream end of the contact region 41 in the blood flow direction illustrated in FIG. 5 to the downstream end of the contact region 41 in the blood flow direction illustrated in FIG. 7. A specific example will be described. When the designation of the arrangement position of the reference surface 50 in the arrangeable range is received from the user via the input interface 330, the setting function 353 moves and arrange the reference surface 50 to the designated arrangement position.

Figure 8:
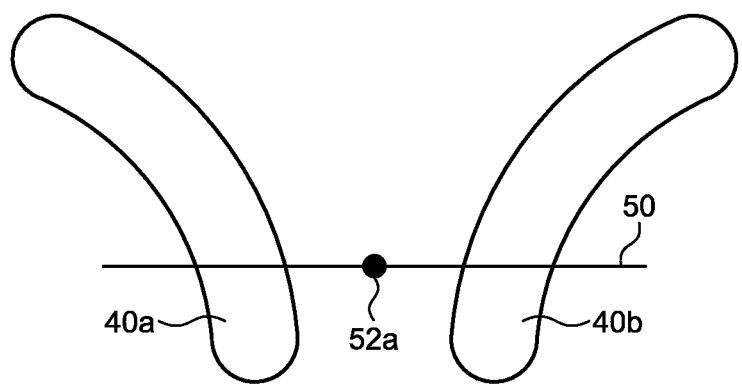
FIG. 8 is a diagram illustrating an example of the arrangement of a reference surface according to the first embodiment.

Next, the case where the two valve leaflet 40a and valve leaflet 40b do not completely contact with each other will be described. In such a case, for example, the setting function 353 moves and arranges the reference surface 50 within a prescribed arrangeable range. FIG. 8 is a diagram illustrating an example of the arrangement of the reference surface 50 according to the first embodiment. For example, the setting function 353 arranges the reference surface 50 as illustrated in FIG. 8. A center 52a illustrated in FIG. 8 on the reference surface 50 between the valve leaflet 40a and the valve leaflet 40b will be described below.

Figure 7:
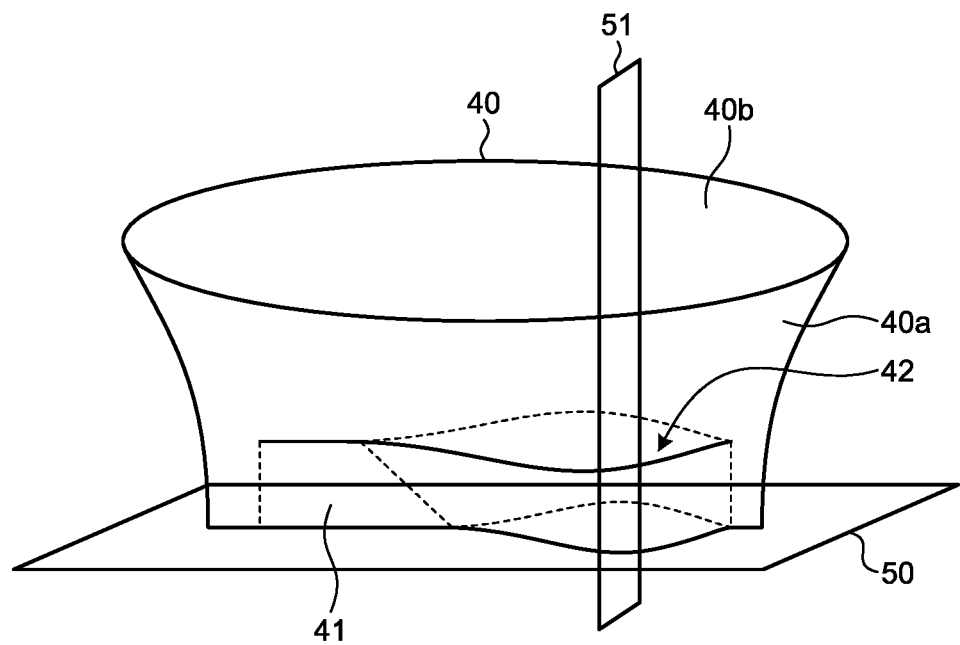
FIG. 7 is a diagram for explaining an example of a process performed by the setting function according to the first embodiment.

When the reference surface 50 is set (arranged), the setting function 353 sets a reference surface (second reference surface) 51 orthogonal to the reference surface 50 and orthogonal to a line segment 40e as illustrated in FIG. 4, FIG. 5, and FIG. 7. The line segment 40e is a line segment that connects a commissure 40c and a commissure 40d of the mitral valve 40. The reference surface 51 is an example of a plane.

In the present embodiment, the reference surface 50 and the reference surface 51 are used in various processes to be described below. Although the method for setting the reference surface 50 and the reference surface 51 with respect to the mitral valve 40 composed of the two valve leaflets 40a and 40b has been described, the setting function 353 can set the reference surface 50 and the reference surface 51 with respect to an aortic valve, a tricuspid valve, and a pulmonary valve composed of three valve leaflets in the same manner.

An example of a method for setting the reference surface 50 and the reference surface 51 with respect to a valve (3-leaflet valve) composed of three valve leaflets will be described. For example, the setting function 353 sets the reference surface 50 with respect to one of the three valve leaflets constituting one 3-leaflet valve in the same manner as the aforementioned method. Furthermore, the setting function 353 sets the reference surface 51 for each combination of two adjacent valve leaflets. That is, the setting function 353 sets one reference surface 50 and three reference surfaces 51 with respect to the 3-leaflet valve.

For example, when the 3-leaflet valve is completely closed, that is, when the three valve leaflets contact with one another at one point (contact point), the setting function 353 derives three line segments that connect the contact point and each of the commissures of the 3-leaflet valve. Then, for each of the three line segments, the setting function 353 sets the reference surface 51 orthogonal to the line segments and orthogonal to the reference surface 50.

Furthermore, for example, when the 3-leaflet valve is not completely closed, the setting function 353 calculates the position of the center of gravity surrounded by the three valve leaflets on the reference surface 50. Then, the setting function 353 derives three line segments that connect the center of gravity and each of the three commissures of the 3-leaflet valve. Then, for each of the three line segments, the setting function 353 sets the reference surface 51 orthogonal to the line segment and orthogonal to the reference surface 50.

When the reference surface 50 and the reference surface 51 are set, the setting function 353 sets a boundary line between two adjacent valve leaflets. The boundary line, for example, indicates the boundary between the two adjacent valve leaflets. The boundary line is an example of a line segment. Hereinafter, an example of the process of setting the boundary line by the setting function 353 will be described employing cases where objects to be processed are the mitral valve 40 (see FIG. 9) and an aortic valve 60 (see FIG. 10 and FIG. 11) as examples.

Figure 9:
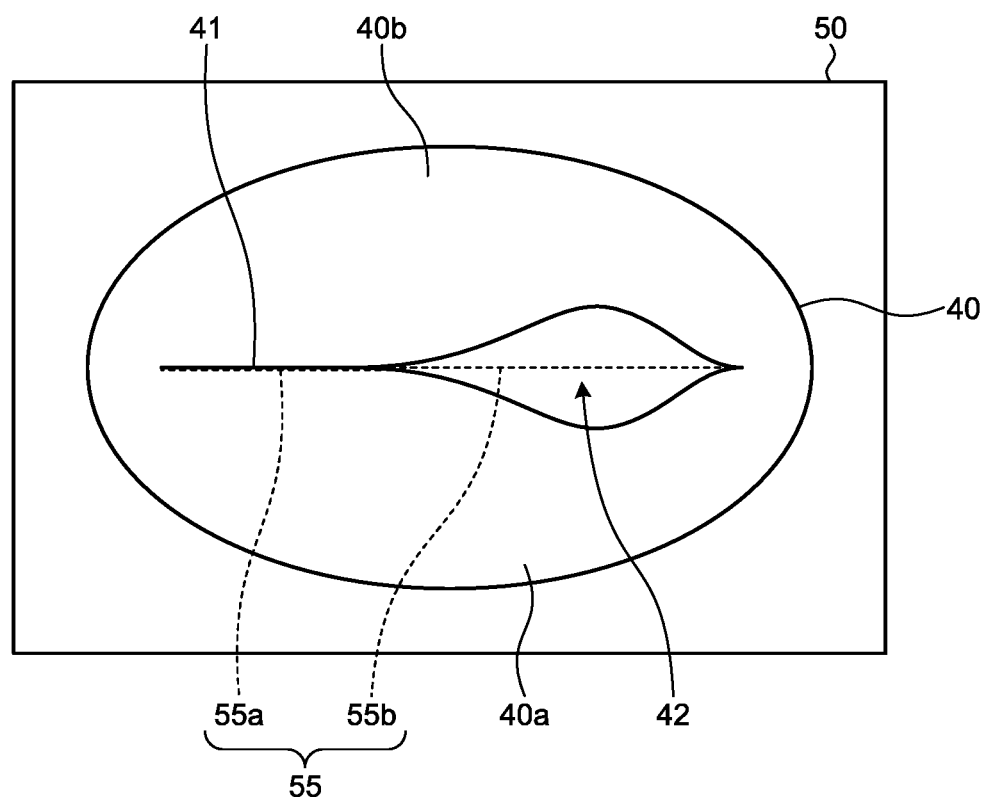
FIG. 9 is a diagram for explaining an example of a process of setting a boundary line by the setting function according to the first embodiment.

FIG. 9 is a diagram for explaining an example of the process of setting a boundary line 55 by the setting function 353 according to the first embodiment. FIG. 9 illustrates the case where the object to be processed is the mitral valve 40. As illustrated in FIG. 9, the setting function 353 sets the boundary line 55 between the valve leaflet 40a and the valve leaflet 40b on the reference surface 50.

The boundary line 55 is a line that connects one end of a boundary line 55a and one end of a virtual boundary line 55b. For example, the setting function 353 sets, on the reference surface 50, the boundary line 55a at a position where the reference surface 50 intersects with the contact region 41. Furthermore, as illustrated in FIG. 8, the setting function 353 sets the virtual boundary line 55b, which passes through the center 52a on the reference surface 50 between the valve leaflet 40a and the valve leaflet 40b, with respect to the reference surface 50. Then, the setting function 353 generates the boundary line 55 by connecting one end of the boundary line 55a and one end of the virtual boundary line 55b. By so doing, the boundary line 55 is set with respect to the reference surface 50.

Figure 10:
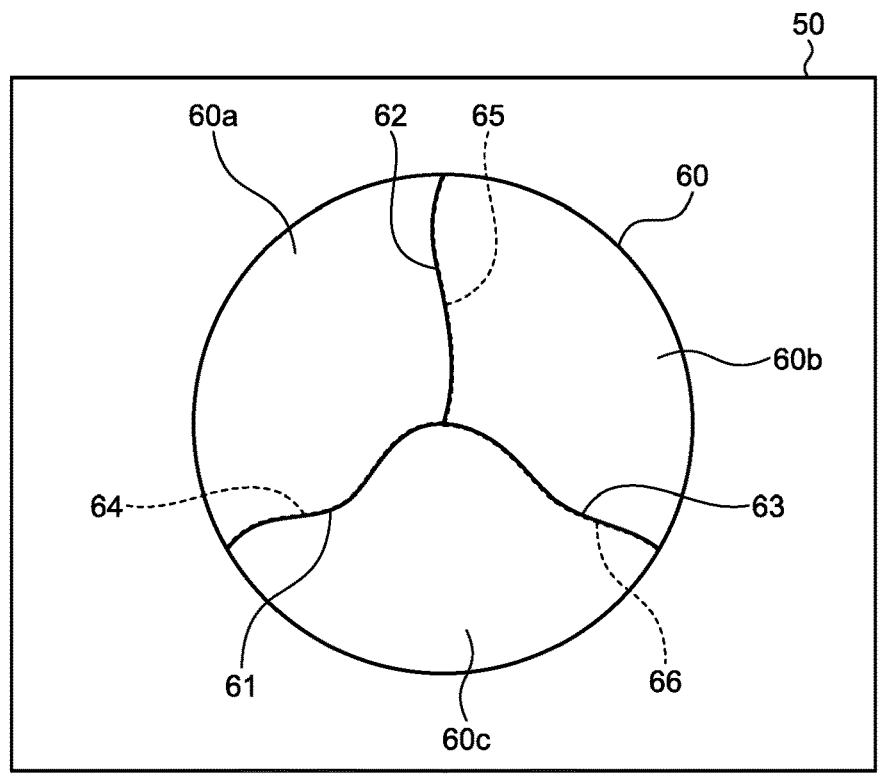
FIG. 10 is a diagram for explaining an example of a process of setting a boundary line by the setting function according to the first embodiment.
Figure 11:
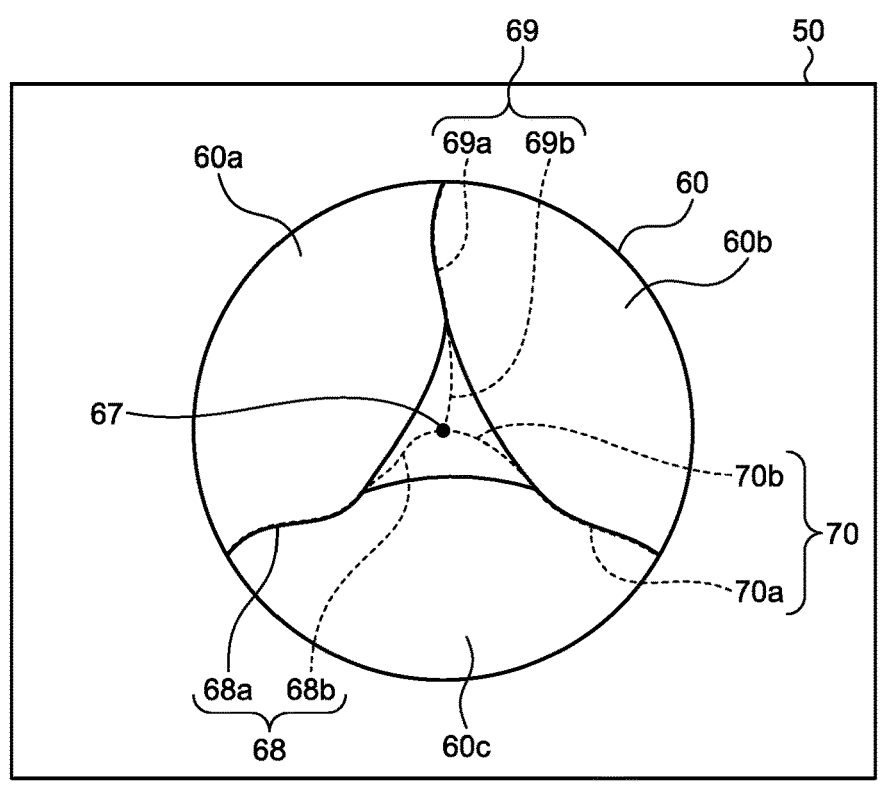
FIG. 11 is a diagram for explaining an example of a process of setting a boundary line by the setting function according to the first embodiment.

FIG. 10 and FIG. 11 are diagrams for explaining an example of the process of setting boundary lines 64 to 66 by the setting function 353 according to the first embodiment. FIG. 10 and FIG. 11 illustrate the cases where the object to be processed is the aortic valve 60 composed of three valve leaflets 60a to 60c. FIG. 10 illustrates a case where the aortic valve 60 is completely closed and FIG. 11 illustrates a case where the aortic valve 60 is not completely closed. That is, FIG. 11 illustrates a case where the valve leaflet 60a and the valve leaflet 60b are partially separated from each other, the valve leaflet 60b and the valve leaflet 60c are partially separated from each other, and the valve leaflet 60c and the valve leaflet 60a are partially separated from each other.

As illustrated in FIG. 10, when the aortic valve 60 is completely closed, the setting function 353 sets the boundary line 64 between the valve leaflet 60c and the valve leaflet 60a on the reference surface 50. For example, the setting function 353 sets, on the reference surface 50, the boundary line 64 at a position where the reference surface 50 intersects a contact region 61. The contact region 61 is a region at which the valve leaflet 60c and the valve leaflet 60a contact with each other.

Similarly, the setting function 353 sets, on the reference surface 50, the boundary line 65 between the valve leaflet 60a and the valve leaflet 60b and the boundary line 66 between the valve leaflet 60b and the valve leaflet 60c. For example, the setting function 353 sets, on the reference surface 50, the boundary line 65 at a position where the reference surface 50 intersects a contact region 62. Furthermore, the setting function 353 sets, on the reference surface 50, the boundary line 66 at a position where the reference surface 50 intersects a contact region 63. The contact region 62 is a region at which the valve leaflet 60a and the valve leaflet 60b contact with each other, and the contact region 63 is a region at which the valve leaflet 60b and the valve leaflet 60c contact with each other.

On the other hand, as illustrated in FIG. 11, when the aortic valve 60 is not completely closed, the setting function 353 calculates a center of gravity 67 of a region surrounded by the three valve leaflets 60a to 60c on the reference surface 50. The region surrounded by the valve leaflets 60a to 60c is a non-contact region where the valve leaflets 60a to 60c do not contact with one another and a non-contact region where the valve leaflets 60a to 60c do not exist.

Then, the setting function 353 sets a boundary line 68 between the valve leaflet 60c and the valve leaflet 60a on the reference surface 50. The boundary line 68 is a line that connects one end of a boundary line 68a and one end of a virtual boundary line 68b. For example, the setting function 353 sets, on the reference surface 50, the boundary line 68a at a position where the reference surface 50 intersects a contact region at which the valve leaflet 60c and the valve leaflet 60a contact with each other. Furthermore, the setting function 353 sets, in the non-contact region, the virtual boundary line 68b, which passes through the center on the reference surface 50 between the valve leaflet 60c and the valve leaflet 60a, with respect to the reference surface 50. Then, the setting function 353 generates the boundary line 68 by connecting one end of the boundary line 68a and one end of the virtual boundary line 68b. The other end of the virtual boundary line 68b is connected to the center of gravity 67. That is, the position of the other end of the virtual boundary line 68b is the same as that of the center of gravity 67. By so doing, the boundary line 68 is set with respect to the reference surface 50.

Similarly, the setting function 353 sets a boundary line 69 between the valve leaflet 60a and the valve leaflet 60b and a boundary line 70 between the valve leaflet 60b and the valve leaflet 60c, on the reference surface 50. The boundary line 69 is a line that connects one end of a boundary line 69a and one end of a virtual boundary line 69b, and the boundary line 70 is a line that connects one end of a boundary line 70a and one end of a virtual boundary line 70b. The other end of the virtual boundary line 69b and the other end of the virtual boundary line 70b are connected to the center of gravity 67.

For example, the setting function 353 sets the boundary line 69 by setting the boundary line 69a and the virtual boundary line 69b on the reference surface 50 by using the valve leaflet 60a and the valve leaflet 60b, in the same manner as the aforementioned method for setting the boundary line 68a and the virtual boundary line 68b on the reference surface 50 by using the valve leaflet 60c and the valve leaflet 60a. Furthermore, the setting function 353 sets the boundary line 70 by setting the boundary line 70a and the virtual boundary line 70b on the reference surface 50 by using the valve leaflet 60b and the valve leaflet 60c in the same manner.

Returning back to the description of FIG. 1, for each of the valve leaflets extracted by the extraction function 352, the measurement function 354 measures the length of a contact region in the valve leaflet at which the valve leaflet and another valve leaflet contact with each other, in the blood flow direction. That is, for each of the valve leaflets, the measurement function 354 measures the length of the contact region in the valve leaflet at which the valve leaflet and the other valve leaflet contact with each other, in the blood flow direction. The length, for example, is an index indicating the degree of close contact in the contact region at which the valve leaflet and the other valve leaflet contact with each other. Hereinafter, an example of the process of measuring the length of the contact region in the blood flow direction by the measurement function 354 will be described employing the case where the object to be processed is the mitral valve 40 as an example.

Figure 12:
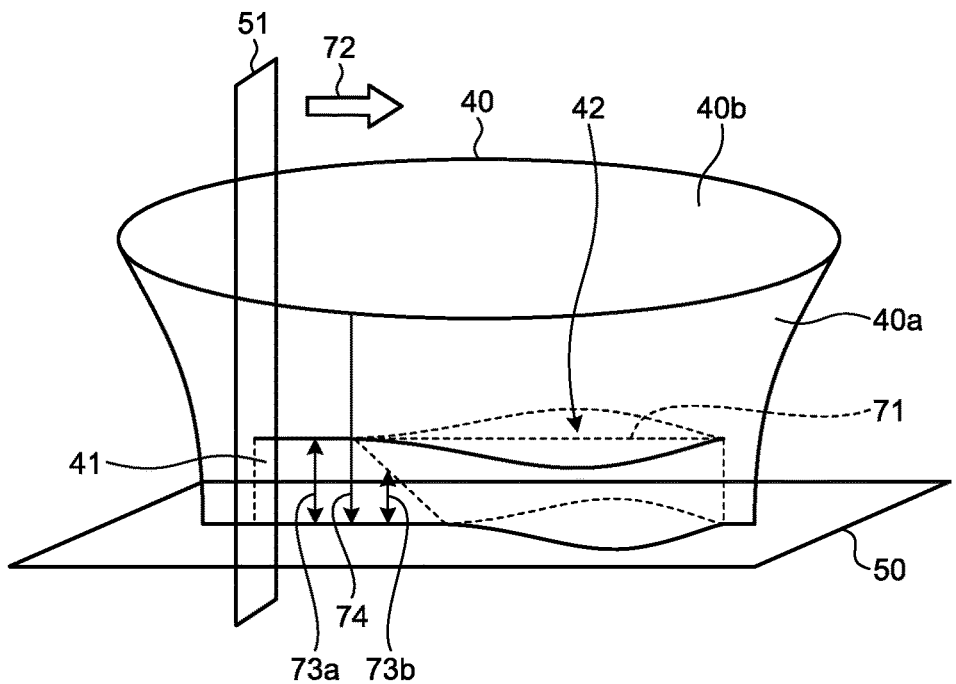
FIG. 12 is a diagram for explaining an example of a process of measuring the length of a contact region in a blood flow direction by a measurement function according to the first embodiment.

FIG. 12 is a diagram for explaining an example of a process of measuring the length of the contact region 41 in a blood flow direction 74 by the measurement function 354 according to the first embodiment. FIG. 12 illustrates a case where the object to be processed is the mitral valve 40. As illustrated in FIG. 12, the measurement function 354 measures the length of the contact region 41 in the blood flow direction 74 at a plurality of positions on a boundary line 71 while moving the reference surface 51 along the boundary line 71 in a direction 72 from one end of the boundary line 71 to the other end of the boundary line 71. The blood flow direction 74 is an example of a predetermined reference direction.

The boundary line 71 is a line set between the valve leaflet 40a and the valve leaflet 40b. Furthermore, in the example of FIG. 12, one end of the boundary line 71 is the left end of the boundary line 71 and the other end of the boundary line 71 is the right end of the boundary line 71.

For example, the measurement function 354 locates the reference surface 51 at each of the positions on the boundary line 71 while moving the reference surface 51. Then, whenever the reference surface 51 is located at each of the positions, the measurement function 354 measures the length of the contact region 41 intersecting with the reference surface 51, on the reference surface 51 in the blood flow direction 74 as the length of the contact region 41 in the blood flow direction 74. That is, the measurement function 354 measures the length of the contact region 41 in a direction intersecting with the reference surface 50 as the length of the contact region 41 in the blood flow direction.

More specifically, the measurement function 354 measures the length of the contact region 41 in a direction approximately perpendicular to the reference surface 50 as the length of the contact region 41 in the blood flow direction. By so doing, the measurement function 354 measures the length of the contact region 41 in the blood flow direction. Furthermore, the measurement function 354 measures the length of the contact region 41 in a direction, which intersects with the boundary line 71, and a direction, which intersects with the reference surface 50, as the length of the contact region 41 in the blood flow direction. For example, the measurement function 354 measures the length of the contact region 41 in a direction, which is orthogonal to the boundary line 71, and a direction, which is orthogonal to the reference surface 50, as the length of the contact region 41 in the blood flow direction. The measurement function 354 may also measure, on the reference surface 51, the length of the contact region 41 intersecting with the reference surface 51, as the length of the contact region 41 in the blood flow direction 74. That is, the measurement function 354 may also measure the length of the contact region 41 on the reference surface 51 as the length of the contact region 41 in the blood flow direction 74.

For example, when the reference surface 51 is located at different positions on the boundary line 71, the measurement function 354 measures a length 73a and a length 73b in the blood flow direction 74 of the contact region 41 as illustrated in FIG. 12. By so doing, the measurement function 354 measures a plurality of lengths corresponding to a plurality of positions on the boundary line 71. That is, the measurement function 354 measures the length of the contact region 41 in the blood flow direction 74 at each position in a direction of the contact region 41 along the boundary line 71 intersecting with the blood flow direction 74. Such a length is also referred to as a "depth". Furthermore, when one end of the boundary line 71 is set as the origin (0), a distance (position) on the boundary line 71 from the origin is also referred to as a "width". Furthermore, the direction along the boundary line 71 is an example of a second direction.

Since the measurement function 354 uses CT image data having a relatively high spatial resolution, the length of the contact region 41 in the blood flow direction can be measured with relatively good accuracy.

Furthermore, the length 73a and the length 73b in the blood flow direction of the contact region 41 at which the valve leaflet 40a and the valve leaflet 40b contact with each other are information indicating the detailed condition of a mitral valve 77, and are valid information as a determination material when the user such as a doctor determines an operation method of the mitral valve 77.

Although the case where, in the mitral valve 40 where one boundary line 71 is set, the length of the contact region 41 in the blood flow direction 74 is measured with respect to the one boundary line 71 has been described, the setting function 353 may also calculate the length of the contact region in the blood flow direction by performing the same process on an aortic valve, a tricuspid valve, and a pulmonary valve, where three boundary lines are set, in the same manner. That is, in the case of the aortic valve, the tricuspid valve, and the pulmonary valve, in each of the three boundary lines, three lengths corresponding to the three boundary lines can be measured using the same manner as the aforementioned method for measuring the length of the contact region 41 in the blood flow direction 74 with respect to the one boundary line 71.

Furthermore, as illustrated in FIG. 12, when a region (opposite region) opposite to the reference surface 51 among all regions of the separation region 42 is not parallel to the reference surface 51, that is, when the opposite region is inclined, an inclination angle of the opposite region relative to the reference surface 51 may be measured by the measurement function 354. Then, the control function 351 may control the display 340 to display the measured inclination angle.

Returning back to the description of FIG. 1, the generation function 355 generates a graph indicating a length at each position (each of the positions) on the boundary line 71, which have been measured by the measurement function 354. Such a graph indicates the distribution of the lengths at the positions on the valve leaflets. Furthermore, the generation function 355 generates image data for display in which the valve leaflets extracted by the extraction function 352 are drawn. Hereinafter, an example of a process of generating the graph and the image data for display by the generation function 355 will be described.

Figure 13:
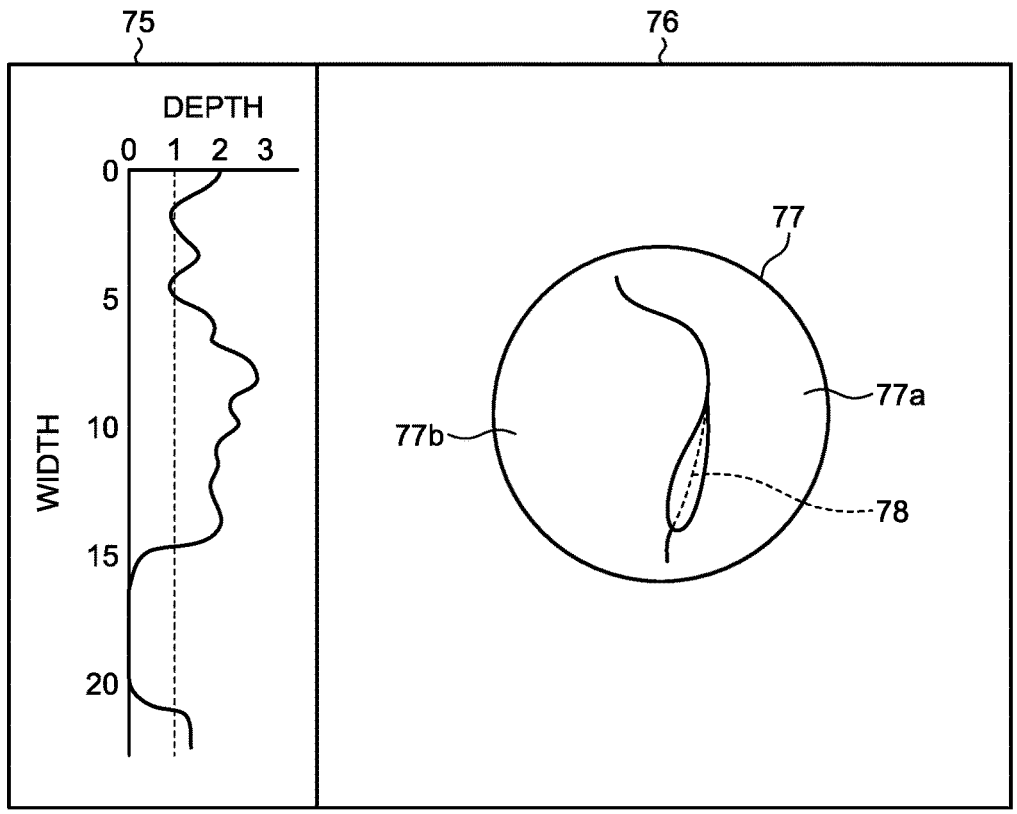
FIG. 13 is a diagram for explaining an example of a process of generating image data of a graph and image data for display by a generation function according to the first embodiment.

FIG. 13 is a diagram for explaining an example of a process of generating image data of a graph and image data for display by the generation function 355 according to the first embodiment. As illustrated in FIG. 13, the generation function 355 generates image data indicating a graph 75 representing the length for each position on a boundary line 78. The length for each position on the boundary line 78 is the length measured by the measurement function 354. Furthermore, the boundary line 78 is a line set between a plurality of valve leaflet 77a and valve leaflet 77b constituting the mitral valve 77. Furthermore, the mitral valve 77 is a valve composed of the valve leaflet 77a and the valve leaflet 77b extracted by the extraction function 352.

In the graph in which a horizontal axis is set as the length (depth) (mm) of a contact region at which the valve leaflet 77a and the valve leaflet 77b contact with each other, in the blood flow direction and a vertical axis is set as the position (width) (mm) on the boundary line 78, the generation function 355 generates image data indicating the graph 75 by plotting a plurality of lengths corresponding to a plurality of positions on the boundary line 78, which have been measured by the measurement function 354.

Furthermore, the generation function 355 generates, as image data for display, image data indicating the multi-planar reconstruction (MPR) image (tomographic image) 76 of the cross-section of the mitral valve 77 cut by the reference surface 50. That is, the generation function 355 generates image data for display including the valve leaflets 77a and 77b from three-dimensional CT image data. This image data is an example of first image data for display. Furthermore, this image data is an example of first tomographic image data. Furthermore, the MPR image 76 is an example of a first tomographic image. The generation function 355 generates image data indicating the boundary line 78. Then, the generation function 355 superimposes the boundary line 78 on the MPR image 76, thereby generating image data indicating the MPR image 76 with the boundary line 78 superimposed thereon. That is, the generation function 355 generates an image, in which the boundary line 78 corresponding to the contact region at which the two valve leaflets 77a and 77b contact with each other is superimposed on the MPR image 76, with respect to the MPR image 76 at a position approximately corresponding to the reference surface 50 in the CT image data.

Since the CT image data has a relatively high spatial resolution, a plurality of valve leaflets are extracted with relatively high accuracy by the extraction function 352. Therefore, the generation function 355, for example, sets a boundary between the valve leaflet 77a illustrated in FIG. 13 and a separation region between the valve leaflet 77a and the valve leaflet 77b to be in a display mode easily recognizable by a user. Similarly, the generation function 355 sets a boundary between the valve leaflet 77b illustrated in FIG. 13 and the separation region to be in a display mode easily recognizable by a user. For example, the generation function 355 generates image data of a red line superimposed on the boundary between the valve leaflet 77a, the valve leaflet 77b, and the separation region, and superimposes the red line indicated by the generated image data on the boundary between the valve leaflet 77a, the valve leaflet 77b, and the separation region.

In the graph 75 of FIG. 13, as indicated by a broken line, a threshold value for determining that the valve leaflet 77a and the valve leaflet 77b are separated from each other is set to 1 mm. In such a case, even though the position on the boundary line 78 where the length of the contact region 41 in the blood flow direction is smaller than 1 mm is the contact region, it is considered to be close to the state in which the valve leaflet 77a and the valve leaflet 77b are separated from each other.

Therefore, the generation function 355 generates image data indicating the graph 75 such that a portion of a curve, which indicates a correspondence relation between the position (width) on the boundary line 78 and the length (depth) of the contact region in the blood flow direction and is smaller than the threshold value, and a portion, which is equal to or more than the threshold value, are in different modes (display modes) in the graph 75. For example, the generation function 355 may also generate the image data indicating the graph 75 such that the portion of the curve smaller than the threshold value and the portion equal to or more than the threshold value are indicated by different colors.

The threshold value is not limited to the aforementioned 1 mm and may be other values. Furthermore, when an instruction for changing the threshold value is received from the user via the input interface 330, the generation function 355 may also change the threshold value on the basis of the instruction.

Figure 14:
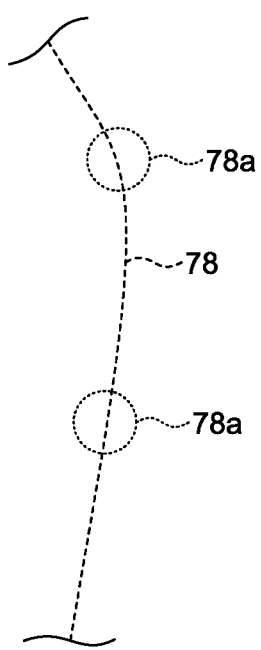
FIG. 14 is an enlargement diagram of a part of a boundary line illustrated in FIG. 13.

FIG. 14 is an enlargement diagram of a part of the boundary line 78 illustrated in FIG. 13. As illustrated in FIG. 14, the generation function 355 generates image data indicating the boundary line 78 such that a portion 78a of the boundary line 78 where the length of the contact region in the blood flow direction is smaller than the threshold value, and a portion (a portion other than the portion 78a) of the boundary line 78, where the length of the contact region in the blood flow direction is equal to or more than the threshold value, are in different modes (display modes).

As described above, the generation function 355 superimposes the boundary line 78 on the MPR image 76. That is, the generation function 355 superimposes the boundary line 78 on the MPR image 76, wherein the boundary line 78 is set between the two adjacent valve leaflet 77a and valve leaflet 77b and has different modes at the portion (the portion other than the portion 78a), where the length of the contact region in the blood flow direction is equal to or more than the threshold value, and the portion 78a where the length of the contact region in the blood flow direction is smaller than the threshold value.

The generation function 355 may also generate a boundary line having more finely different display modes depending on the length of the contact region in the blood flow direction by using a plurality of threshold values instead of one threshold value.

Figure 15:
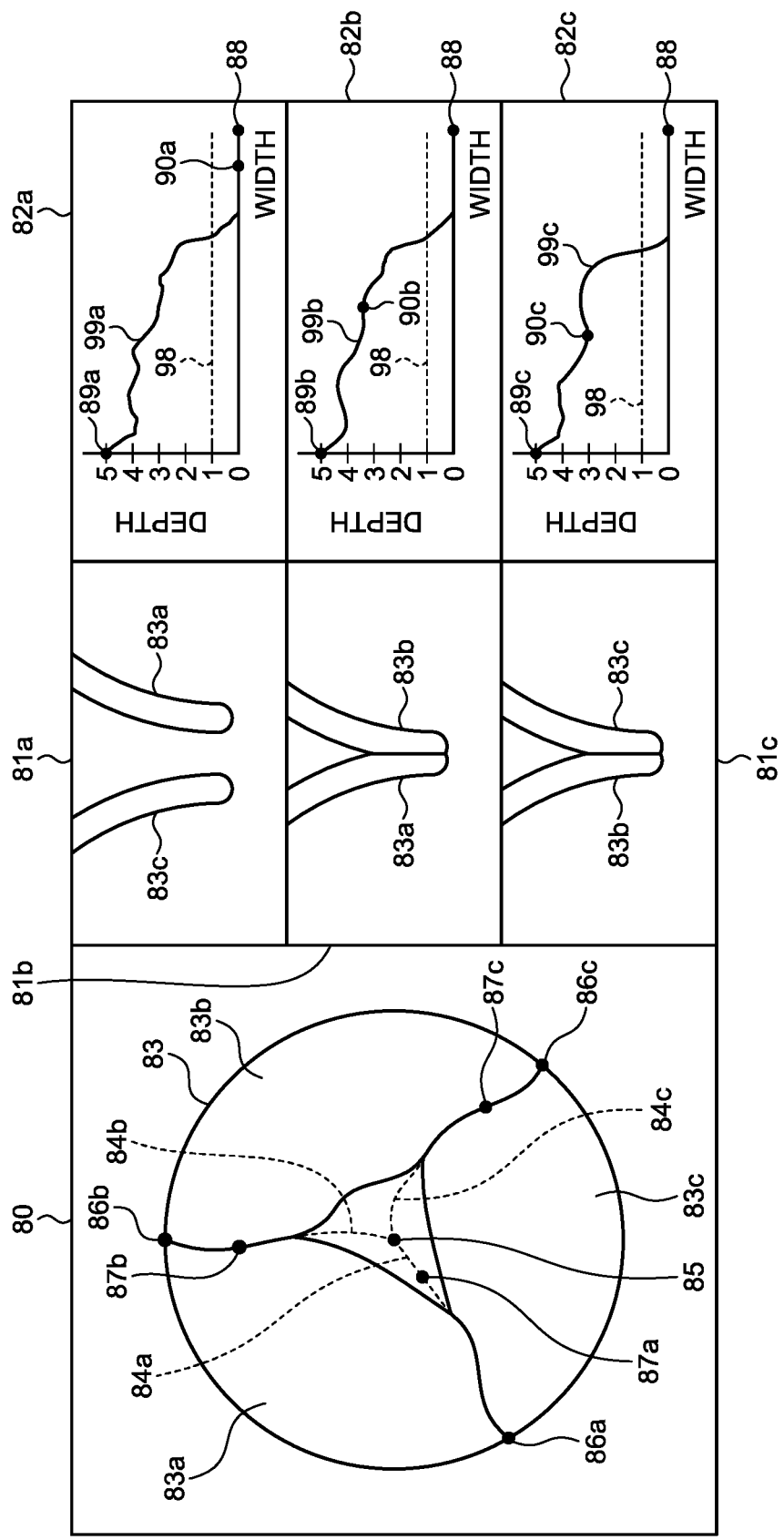
FIG. 15 is a diagram for explaining an example of a process of generating image data of another graph and another image data for display by the generation function according to the first embodiment.

FIG. 15 is a diagram for explaining an example of a process of generating image data of another graph and another image data for display by the generation function 355 according to the first embodiment. As illustrated in FIG. 15, the generation function 355 generates image data indicating an MPR image 80 of the cross-section of an aortic valve 83 cut by the reference surface 50, as image data for display. The aortic valve 83 is a valve composed of a plurality of valve leaflets 83a to 83c extracted by the extraction function 352. That is, the generation function 355 generates image data for display including the valve leaflets 83a to 83c from the three-dimensional CT image data. This image data is an example of first image data for display.

Then, the generation function 355 generates image data indicating a boundary line 84a, image data indicating a boundary line 84b, and image data indicating a boundary line 84c. The boundary line 84a is a line set between the valve leaflet 83c and the valve leaflet 83a. Furthermore, the boundary line 84b is a line set between the valve leaflet 83a and the valve leaflet 83b. Furthermore, the boundary line 84c is a line set between the valve leaflet 83b and the valve leaflet 83c.

Furthermore, the generation function 355 generates image data indicating a mark 85 of the center of gravity. The center of gravity described herein is the center of gravity of a non-contact region (non-existence region) surrounded by the three valve leaflet 83a, valve leaflet 83b, and valve leaflet 83c on the reference surface 50.

Furthermore, the generation function 355 generates image data indicating a mark 86a at an end of a side opposite to the side of the center of gravity of the boundary line 84a. Furthermore, the generation function 355 generates image data indicating a mark 86b at an end of a side opposite to the side of the center of gravity of the boundary line 84b. Furthermore, the generation function 355 generates image data indicating a mark 86c at an end of a side opposite to the side of the center of gravity of the boundary line 84c.

Furthermore, the generation function 355 generates image data indicating a mark 87a movable on the boundary line 84a. Furthermore, the generation function 355 generates image data indicating a mark 87b movable on the boundary line 84b. Furthermore, the generation function 355 generates image data indicating a mark 87c movable on the boundary line 84c.

Then, the generation function 355 superimposes the boundary lines 84a to 84c and the marks 85, 86a to 86c, and 87a to 87c on the MPR image 80. In this way, the generation function 355 generates the image data indicating the MPR image 80 with the boundary lines 84a to 84c and the marks 85, 86a to 86c, and 87a to 87c superimposed thereon.

Furthermore, the generation function 355 generates image data indicating an MPR image 81a of the cross-section of the aortic valve 83 passing through the mark 87a on the boundary line 84a and orthogonal to the boundary line 84a. Furthermore, the generation function 355 generates image data indicating an MPR image 81b of the cross-section of the aortic valve 83 passing through the mark 87b on the boundary line 84b and orthogonal to the boundary line 84b. Furthermore, the generation function 355 generates image data indicating an MPR image 81c of the cross-section of the aortic valve 83 passing through the mark 87c on the boundary line 84c and orthogonal to the boundary line 84c.

As illustrated in FIG. 15, the MPR image 81a indicates a contact state of the valve leaflet 83c and the valve leaflet 83a. Similarly, the MPR image 81b indicates a contact state of the valve leaflet 83a and the valve leaflet 83b, and the MPR image 81c indicates a contact state of the valve leaflet 83b and the valve leaflet 83c.

For example, the MPR image 81a indicates a state in which the valve leaflet 83c and the valve leaflet 83a are separated from each other. Furthermore, the MPR image 81b indicates a state in which the valve leaflet 83a and the valve leaflet 83b contact with each other. Furthermore, the MPR image 81c indicates a state in which the valve leaflet 83b and the valve leaflet 83c contact with each other.

Furthermore, the generation function 355 generates image data indicating a graph 82a representing the length of the contact region in the blood flow direction for each position on the boundary line 84a. Furthermore, the generation function 355 generates image data indicating a graph 82b representing the length of the contact region in the blood flow direction for each position on the boundary line 84b. Furthermore, the generation function 355 generates image data indicating a graph 82c representing the length of the contact region in the blood flow direction for each position on the boundary line 84c. The length of the contact region in the blood flow direction for each position on the boundary line 84a, the length of the contact region in the blood flow direction for each position on the boundary line 84b, and the length of the contact region in the blood flow direction for each position on the boundary line 84c are measured by the measurement function 354.

In the graph 82a, a curve 99a indicates a correspondence relation between a position (width) on the boundary line 84a and the length (depth) of the contact region at which the valve leaflet 83c and the valve leaflet 83a contact with each other, in the blood flow direction.

In the graph 82a, a mark 89a corresponds to the mark 86a at the end of the boundary line 84a. That is, in the graph 82a, the mark 89a is arranged at a position indicating the position (width: origin (0)) of the mark 86a on the boundary line 84a and a length (depth: 5 mm) corresponding to the position of the mark 86a on the boundary line 84a.

Furthermore, in the graph 82a, a mark 88 corresponds to the mark 85 indicating the center of gravity. That is, in the graph 82a, the mark 88 is arranged at a position indicating the position of the center of gravity on the boundary line 84a and a length (depth: 0 mm) corresponding to the position of the center of gravity on the boundary line 84a.

Furthermore, in the graph 82a, a mark 90a corresponds to the mark 87a. That is, the mark 90a is arranged on the curve 99a to indicate the same position as that of the mark 87a on the boundary line 84a.

The same applies also to a curve 99b, a mark 89b, a mark 88, and a mark 90b in the graph 82b, and a curve 99c, a mark 89c, a mark 88, and a mark 90c in the graph 82c. That is, the curve 99b indicates a correspondence relation between the positions on the boundary line 84b and the lengths of the contact region at which the valve leaflet 83a and the valve leaflet 83b contact with each other, in the blood flow direction. The mark 89b corresponds to the mark 86b at the end of the boundary line 84b. In the graph 82b, the mark 88 indicates the position of the center of gravity on the boundary line 84b and a length (depth: 0 mm) corresponding to the position of the center of gravity on the boundary line 84b. The mark 90b corresponds to the mark 87b.

Furthermore, the curve 99c indicates a correspondence relation between a position on the boundary line 84c and the length of the contact region at which the valve leaflet 83b and the valve leaflet 83c contact with each other, in the blood flow direction. The mark 89c corresponds to the mark 86c at the end of the boundary line 84c. In the graph 82c, the mark 88 indicates the position of the center of gravity on the boundary line 84c and a length (depth: 0 mm) corresponding to the position of the center of gravity on the boundary line 84c. The mark 90c corresponds to the mark 87c.

In the graph 82a, a threshold value 98 for determining that the valve leaflet 83c and the valve leaflet 83a are separated from each other is set to 1 mm. Therefore, the generation function 355 may also generate image data indicating the graph 82a such that a portion of the curve 99a smaller than the threshold value 98 and a portion equal or more than the threshold value 98 have different modes in the graph 82a. The same applies also to the graph 82b and the graph 82c.

Also in the example of FIG. 15, similarly to the example of FIG. 13, the threshold value is not limited to the aforementioned 1 mm and may be other values. Furthermore, when an instruction for changing the threshold value is received from the user, the generation function 355 may also change the threshold value on the basis of the instruction.

For example, when the image data indicating the graph 75 illustrated in FIG. 13 and the image data indicating the MPR image 76 with the boundary line 78 superimposed thereon are generated by the generation function 355, the control function 351 transmits the image data indicating the graph 75 and the image data indicating the MPR image 76 with the boundary line 78 superimposed thereon to the display 340. Then, as illustrated in FIG. 13, the control function 351 controls the display 340 to display the graph 75 and the MPR image 76 with the boundary line 78 superimposed thereon.

That is, the control function 351 controls the display 340 to display the length of the contact region in the blood flow direction, where the valve leaflet 77a and the valve leaflet 77b contact with each other, at each position in the contact region and at each position in a direction along the boundary line 78 intersecting with the blood flow direction. As described above, the control function 351 allows the display 340 to graphically display the distribution of the lengths at the positions on the boundary line 78. Furthermore, the control function 351 controls the display 340 to display the MPR image 76 for display, in which the valve leaflet 77a and the valve leaflet 77b are drawn, together with the length of the contact region in the blood flow direction. That is, the control function 351 allows the display 34 to display an image, in which the boundary line 78 corresponding to the contact region where the two valve leaflets 77a and 77b contact with each other is superimposed on the MPR image 76, with respect to the MPR image 76. The MPR image 76 for display is an example of a first image for display. Furthermore, the direction along the boundary line 78 is an example of a second direction.

As described above, the medical image processing apparatus 300 according to the first embodiment displays the length of the contact region at which the valve leaflet 77a and the valve leaflet 77b contact with each other, in the blood flow direction. The length of the contact region at which the valve leaflet 77a and the valve leaflet 77b contact with each other, in the blood flow direction is information indicating the detailed condition of the mitral valve 77, and is useful information as a determination material when the user such as a doctor determines an operation method of the mitral valve 77. Thus, according to the medical image processing apparatus 300, it is possible to allow the user to understand the detailed condition of the mitral valve 77. Moreover, as a consequence, according to the medical image processing apparatus 300, it is possible to support the determination of the user regarding the operation method of the mitral valve 77. For example, the user can intuitively specify a portion of the mitral valve 77 that requires an operation. Therefore, it is possible to shorten time required for planning the operation of the mitral valve 77.

Furthermore, the medical image processing apparatus 300 allows the display 340 to display the MPR image 76 with the boundary line 78 superimposed thereon having different modes at the portion (the portion other than the portion 78a), where the length of the contact region in the blood flow direction is equal to or more than the threshold value, and the portion 78a where the length of the contact region in the blood flow direction is smaller than the threshold value. Therefore, according to the medical image processing apparatus 300, when the threshold value is made larger than 0, it is possible to allow the user to easily understand the contact region between the valve leaflet 77a and the valve leaflet 77b, which is considered to be close to the state of being separated as well as the separation region where the valve leaflet 77a and the valve leaflet 77b are separated from each other.

When the reference surface 50 is moved by the user's manipulation, the generation function 355 generates a new MPR image 76 on the basis of the position of the moved reference surface 50. Then, the control function 351 updates the MPR image 76 being displayed on the display 340 with the new MPR image 76.

Furthermore, for example, a description will be given for a case where the generation function 355 generates image data indicating the MPR image 80 with the boundary lines 84a to 84c and the marks 85, 86a to 86c, and 87a to 87c superimposed thereon illustrated in FIG. 15, each piece of image data of the MPR images 81a to 81c, and each piece of image data of the graphs 82a to 82c. In such a case, the control function 351 transmits these pieces of image data to the display 340. Then, as illustrated in FIG. 15, the control function 351 controls the display 340 to display the MPR image 80 with the boundary lines 84a to 84c and the marks 85, 86a to 86c, and 87a to 87c superimposed thereon, the MPR images 81a to 81c, and the graphs 82a to 82c.

The mark 87a displayed on the display 340 is movable on the boundary line 84a by the user's manipulation via the input interface 330. Similarly, the mark 87b is movable on the boundary line 84b by a user's manipulation, and the mark 87c is movable on the boundary line 84c by the user's manipulation. For example, the generation function 355 moves the marks 87a to 87c to positions designated by the user.

Therefore, the generation function 355 generates image data indicating a new MPR image 81a depending on the position of the moved mark 87a. Similarly, the generation function 355 generates image data indicating a new MPR image 81b depending on the position of the moved mark 87b, and generates image data indicating a new MPR image 81c depending on the position of the moved mark 87c. That is, the generation function 355 generates the image data indicating the new MPR images 81a to 81c in response to a change in the positions of the marks 87a to 87c.

As described above, the generation function 355 receives the designation of the position on the boundary line 84a, and generates image data for display indicating the MPR image 81a for display in which the designated position is included and the two adjacent valve leaflet 83c and valve leaflet 83a are drawn. Similarly, the generation function 355 receives the designation of the position on the boundary line 84b, and generates image data for display indicating the MPR image 81b for display in which the designated position is included and the two adjacent valve leaflet 83a and valve leaflet 83b are drawn. Furthermore, the generation function 355 receives the designation of the position on the boundary line 84c, and generates image data for display indicating an MPR image 81c for display in which the designated position is included and the two adjacent valve leaflet 83b and valve leaflet 83c are drawn.

The MPR images 81a to 81c are examples of a second image for display. Furthermore, the MPR images 81a to 81c are examples of a second tomographic image. The image data of each of the MPR images 81a to 81c is an example of a second image data for display. Furthermore, the image data of each of the MPR images 81a to 81c is an example of second tomographic image data.

Then, the control function 351 controls the display 340 to display the MPR image 81a indicated by the image data of the MPR image 81a. Similarly, the control function 351 controls the display 340 to display the MPR image 81b indicated by the image data of the MPR image 81b. The control function 351 controls the display 340 to display the MPR image 81c indicated by the image data of the MPR image 81c. A specific example will be described. The control function 351 controls the display 340 such that the MPR images 81a to 81c being displayed are updated with the new MPR images 81a to 81c. As described above, in response to a change in the positions of the marks 87a to 87c, the medical image processing apparatus 300 updates the MPR images 81a to 81c to be displayed.

Consequently, a user can easily understand the contact state of the valve leaflet 83c and the valve leaflet 83a, the contact state of the valve leaflet 83a and the valve leaflet 83b, and the contact state of the valve leaflet 83b and the valve leaflet 83c at various positions only by moving the marks 87a to 87c.

Furthermore, depending on the position of the moved mark 87a, the generation function 355 generates image data indicating a new graph 82a in which the position of the mark 90a on the curve 99a is changed to the same position as that of the moved mark 87a. Furthermore, depending on the position of the moved mark 87b, the generation function 355 generates image data indicating a new graph 82b in which the position of the mark 90b on the curve 99b is changed to the same position as that of the moved mark 87b. Furthermore, depending on the position of the moved mark 87c, the generation function 355 generates image data indicating a new graph 82c in which the position of the mark 90c on the curve 99c is changed to the same position as that of the moved mark 87c.

That is, in response to a change in the positions of the marks 87a to 87c, the generation function 355 generates the new graphs 82a to 82c. Then, the control function 351 controls the display 340 such that the graphs 82a to 82c being displayed are updated with the new graphs 82a to 82c. As described above, in response to a change in the positions of the marks 87a to 87c, the medical image processing apparatus 300 updates the graphs 82a to 82c to be displayed.

Furthermore, when the reference surface 50 is moved by the user's manipulation, the generation function 355 generates a new MPR image 80 on the basis of the position of the moved reference surface 50. Then, the control function 351 updates the MPR image 80 being displayed on the display 340 with the new MPR image 80.

The medical image processing apparatus 300 according to the first embodiment displays the length of the contact region at which the valve leaflet 83c and the valve leaflet 83a contact with each other, in the blood flow direction, the length of the contact region at which the valve leaflet 83a and the valve leaflet 83b contact with each other, in the blood flow direction, and the length of the contact region at which the valve leaflet 83b and the valve leaflet 83c contact with each other, in the blood flow direction. Thus, according to the medical image processing apparatus 300, it is possible to allow the user to understand the detailed condition of the aortic valve 83. Furthermore, according to the medical image processing apparatus 300, it is possible to support the determination of the user regarding the operation method of the aortic valve 83.

Figure 16:
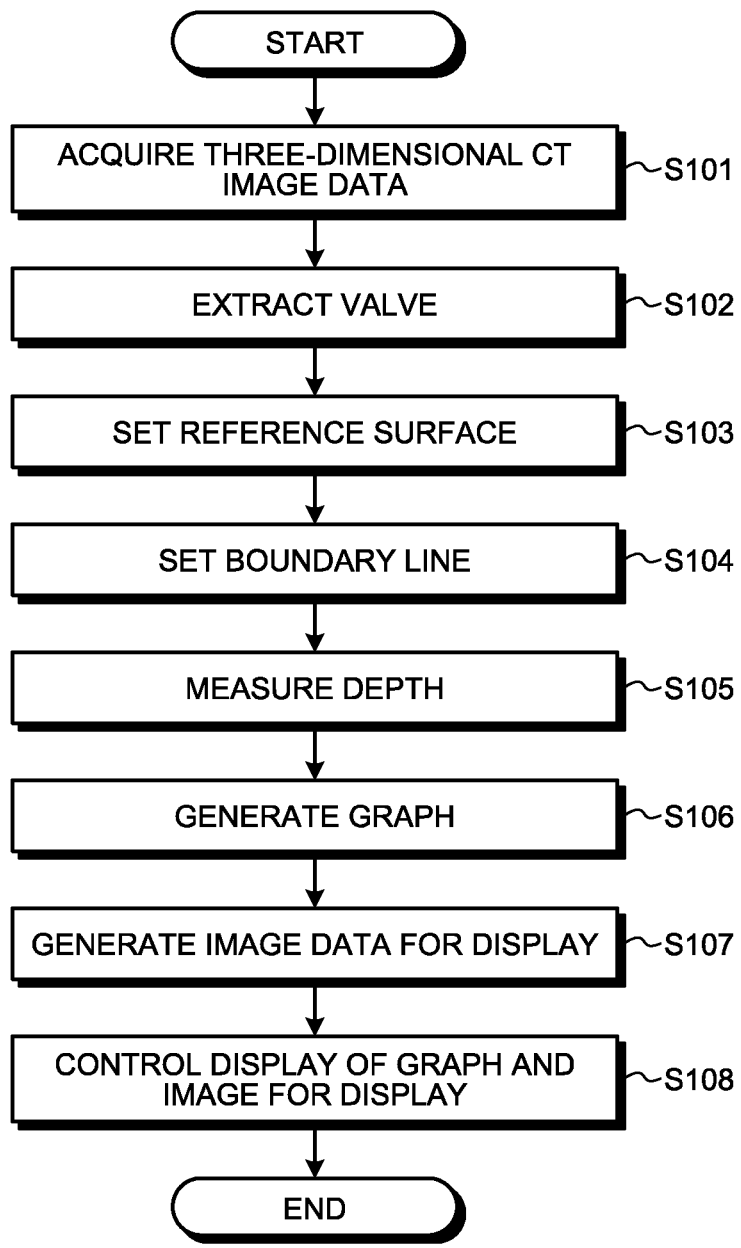
FIG. 16 is a flowchart illustrating an example of the flow of a process performed by processing circuitry according to the first embodiment.

FIG. 16 is a flowchart illustrating an example of the flow of a process performed by the processing circuitry 350 according to the first embodiment. Such a process, for example, is performed by each of the functions 351 to 355 of the processing circuitry 350 when an instruction for performing the process is received from the input interface 330.

As illustrated in FIG. 16, the extraction function 352 acquires the three-dimensional CT image data or the four-dimensional CT image data stored in the memory 320 (step S101). When the four-dimensional CT image data is acquired, the extraction function 352 acquires the three-dimensional CT image data of one time phase from the three-dimensional CT image data of the time phases constituting the four-dimensional CT image data.

Then, the extraction function 352 extracts each of the valve leaflets constituting the valve of the heart of the subject from the three-dimensional CT image data (step S102). Then, for the valve leaflets extracted by the extraction function 352, the setting function 353 sets the reference surface 50 and the reference surface 51 related to the valve leaflets (step S103).

Then, the setting function 353 sets a boundary line between two adjacent valve leaflets (step S104). Then, for each of the valve leaflets, the measurement function 354 measures the length of a contact region in the valve leaflet at which the valve leaflet and another valve leaflet are contact with each other, in the blood flow direction (step S105). Then, the generation function 355 generates image data indicating a graph representing the length of the contact region in the blood flow direction for each position on the boundary line set between the valve leaflets constituting the valve (step S106).

Then, the generation function 355 generates, as image data for display, image data indicating an MPR image of the cross-section of the valve cut by the reference surface 50 (step S107). Then, the control function 351 controls the display 340 to display the graph and the image for display (step S108), and ends the process.

Steps S101 and S102 illustrated in FIG. 16 are steps corresponding to the extraction function 352. Steps S101 and S102 are steps that are implemented by the extraction function 352 when the processing circuitry 350 calls and executes a computer program corresponding to the extraction function 352 from the memory 320. Steps S103 and S104 are steps corresponding to the setting function 353. Steps S103 and S104 are steps that are implemented by the setting function 353 when the processing circuitry 350 calls and executes a computer program corresponding to the setting function 353 from the memory 320.

Step S105 is a step corresponding to the measurement function 354. Step S105 is a step that is implemented by the measurement function 354 when the processing circuitry 350 calls and executes a computer program corresponding to the measurement function 354 from the memory 320.

Steps S106 and S107 are steps corresponding to the generation function 355. Steps S106 and S107 are steps that are implemented by the setting function 353 when the processing circuitry 350 calls and executes a computer program corresponding to the generation function 355 from the memory 320. Step S108 is a step that is implemented by the control function 351 when the processing circuitry 350 calls and executes a computer program corresponding to the control function 351 from the memory 320.

So far, the medical image processing apparatus 300 according to the first embodiment has been described. According to the medical image processing apparatus 300, it is possible to allow the user to understand the detailed condition of the valves as described above.

First Modification Example of First Embodiment

A first embodiment has described the case where, for the valve leaflets extracted by the extraction function 352, the setting function 353 sets the reference surface 50 related to the valve leaflets and intersecting with the blood flow direction. However, for at least one of the valve leaflets, the setting function 353 may set the reference surface 50 related to the at least one valve leaflet and intersecting with the blood flow direction.

Furthermore, the first embodiment has described the case where, for each of the valve leaflets, the measurement function 354 measures the length of the contact region at which the valve leaflet and another valve leaflet contact with each other, in the blood flow direction. However, for at least one of the valve leaflets, the measurement function 354 may measure the length of the contact region at which the one valve leaflet and the other valve leaflet contact with each other, in the blood flow direction.

Second Modification Example of First Embodiment

The medical image processing apparatus 300 may measure information indicating the detailed condition of valves other than the length of the contact region in the blood flow direction. Accordingly, a case of measuring information indicating the detailed condition of other valves will be described. Hereinafter, in a second modification example to a sixth modification example of the first embodiment, five pieces of information indicating the detailed condition of the valves other than the length of the contact region in the blood flow direction will be described.

The medical image processing apparatus 300 according to each of the second modification example to the sixth modification example of the first embodiment performs the same processes as those of the medical image processing apparatus 300 according to the aforementioned first embodiment and then performs the following processes.

Figure 17:
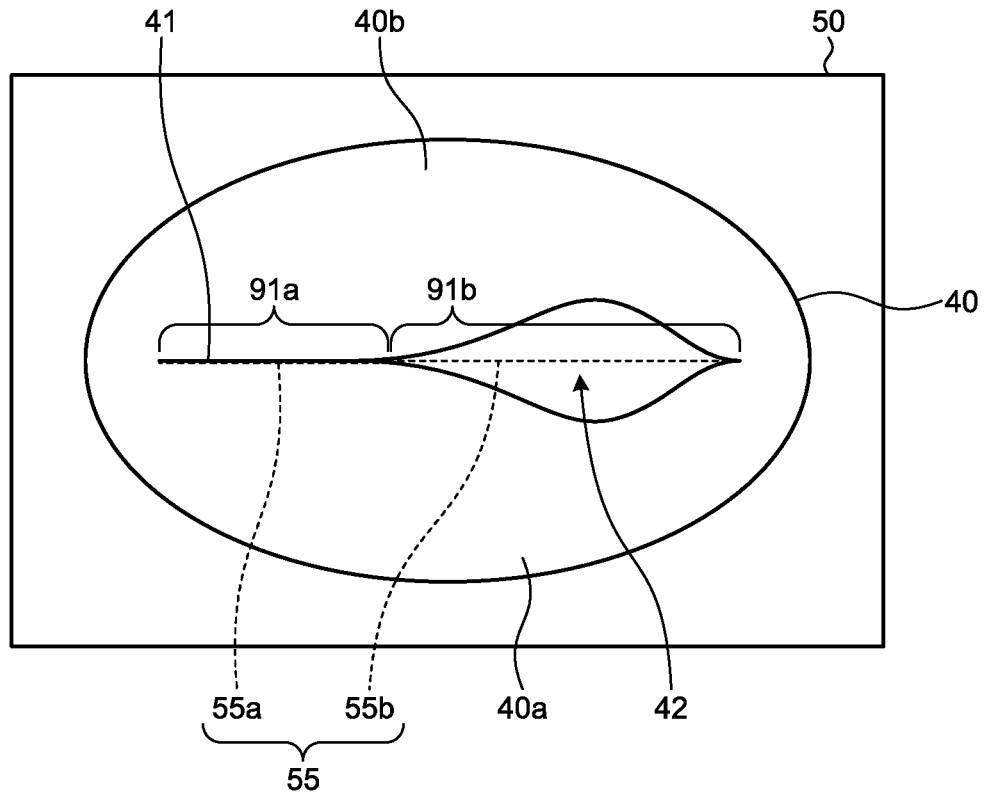
FIG. 17 is a diagram for explaining an example of a process performed by a second modification example and a third modification example.

In the description of the second modification example to the sixth modification example of the first embodiment, the same components as those of the first embodiment are denoted by the same reference numerals and a description thereof will be omitted. FIG. 17 is a diagram for explaining an example of a process performed by the second modification example and the third modification example.

First, the second modification example of measuring information indicating the detailed condition of a first valve will be described. As illustrated in FIG. 17, the measurement function 354 measures a length 91a of the boundary line 55a. That is, the measurement function 354 calculates the length 91a in a direction along the boundary line 55a of the contact region 41 at which the valve leaflet 40a and the valve leaflet 40b contact with each other. The direction along the boundary line 55a is an example of a second direction.

For at least one of the valve leaflets extracted by the extraction function 352, it is sufficient if the measurement function 354 calculates the length of a contact region at which the at least one valve leaflet and another valve leaflet contact with each other, in a direction along a boundary line.

Then, the control function 351 controls the display 340 to display the length of the contact region, which is measured by the measurement function 354, in the direction along the boundary line. For example, the control function 351 controls the display 340 to display the length 91a of the contact region 41 in the direction along the boundary line 55a.

Third Modification Example of First Embodiment

Next, the third modification example of measuring information indicating the detailed condition of a second valve will be described. As illustrated in FIG. 17, the measurement function 354 measures a length 91b in a direction along the virtual boundary line 55b of the separation region 42 between a part of the valve leaflet 40a and a part of the valve leaflet 40b separated from each other. The direction along the virtual boundary line 55b is an example of a second direction.

For at least one of the valve leaflets extracted by the extraction function 352, it is sufficient if the measurement function 354 calculates the length of a separation region between the at least one valve leaflet and another valve leaflet separated from each other, in a direction along a boundary line.

Then, the control function 351 controls the display 340 to display the length of the separation region measured by the measurement function 354, in the direction along the boundary line. For example, the control function 351 controls the display 340 to display the length 91b of the separation region 42 in the direction along the virtual boundary line 55b.

Fourth Modification Example of First Embodiment

Figure 18:
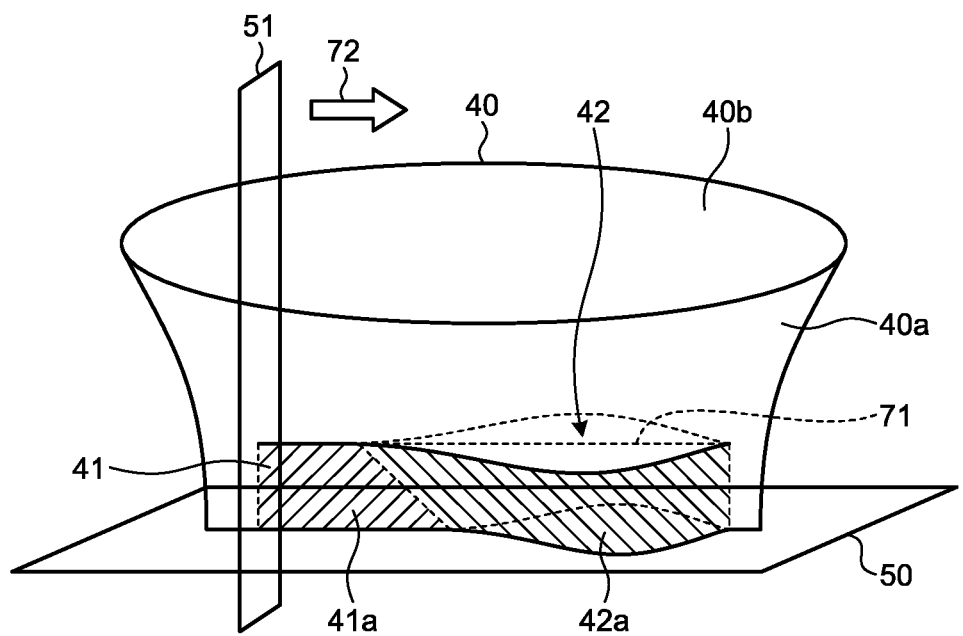
FIG. 18 is a diagram for explaining an example of a process performed by a fourth modification example and a fifth modification example.

Next, the fourth modification example of measuring information indicating the detailed condition of a third valve will be described. FIG. 18 is a diagram for explaining an example of a process performed by the fourth modification example and the fifth modification example. As illustrated in FIG. 18, the measurement function 354 measures a contact area 41a in the contact region 41 where the valve leaflet 40a and the valve leaflet 40b contact with each other. An example of the measurement method of the contact area 41a will be described. For example, the measurement function 354 measures, as the contact area 41a, an integration value obtained by integrating a plurality of lengths (the lengths in the blood flow direction of the contact region 41) corresponding to a plurality of positions on the measured boundary line 71 in a direction along the boundary line 71.

It is sufficient if, for at least one of the valve leaflets extracted by the extraction function 352, the measurement function 354 measures a contact area in a contact region where the at least one valve leaflet and another valve leaflet contact with each other.

Then, the control function 351 controls the display 340 to display the contact area measured by the measurement function 354.

Figure 19:
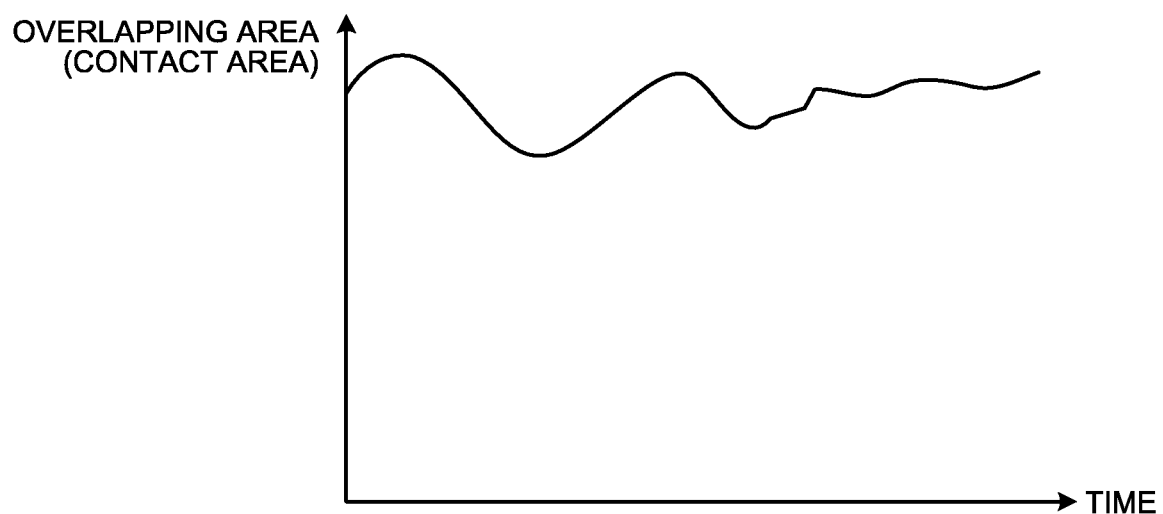
FIG. 19 is a diagram for explaining an example of a process performed by the fourth modification example.

So far, the case where the measurement function 354 measures a contact area in one time phase by using the three-dimensional CT image data of one time phase has been described. However, by using each piece of the three-dimensional CT image data of the time phases constituting the four-dimensional CT image data, the measurement function 354 may also measure a contact area in each of the time phases. FIG. 19 is a diagram for explaining an example of a process performed by the fourth modification example. In such a case, as illustrated in FIG. 19, the generation function 355 generates image data indicating a graph, in which a horizontal axis is set as time (time phase) and a vertical axis is set as an overlapping area (contact area) and which represents a contact area for each time phase, by using the contact areas in the time phases measured by the measurement function 354.

Then, the control function 351 transmits the image data generated by the generation function 355 to the display 340 and controls the display 340 to display the graph indicated by the image data.

Fifth Modification Example of First Embodiment

Next, the fifth modification example of measuring information indicating the detailed condition of a fourth valve will be described. As illustrated in FIG. 18, the measurement function 354 measures an area of "a part of the aforementioned valve leaflet 40a" forming the separation region 42 as a separation area 42a.

For example, the measurement function 354 moves the reference surface 51 so as to follow the boundary line 71 in the direction 72 from one end of the boundary line 71 to the other end of the boundary line 71 within the separation region 42 and measures the length of the valve leaflet 40a, which intersects with the reference surface 51, on the reference surface 51 at the positions on the boundary line 71.

For example, the measurement function 354 locates the reference surface 51 at each of the positions on the boundary line 71 within the separation region 42 while moving the reference surface 51. Then, when the reference surface 51 is located at each of the positions, the measurement function 354 measures the length of the valve leaflet 40a, which intersects with the reference surface 51, on the reference surface 51 within the separation region 42.

Then, the measurement function 354 measures, as the separation area 42a, an integration value obtained by integrating a plurality of lengths (the lengths of the valve leaflet 40a on the reference surface 51) corresponding to the positions on the boundary line 71 in the direction along the boundary line 71. Then, the control function 351 controls the display 340 to display the separation area 42a measured by the measurement function 354.

It is sufficient if, for at least one of the valve leaflets extracted by the extraction function 352, the measurement function 354 measures a separation area in a separation region between the at least one valve leaflet and another valve leaflet separated from each other.

Figure 20:
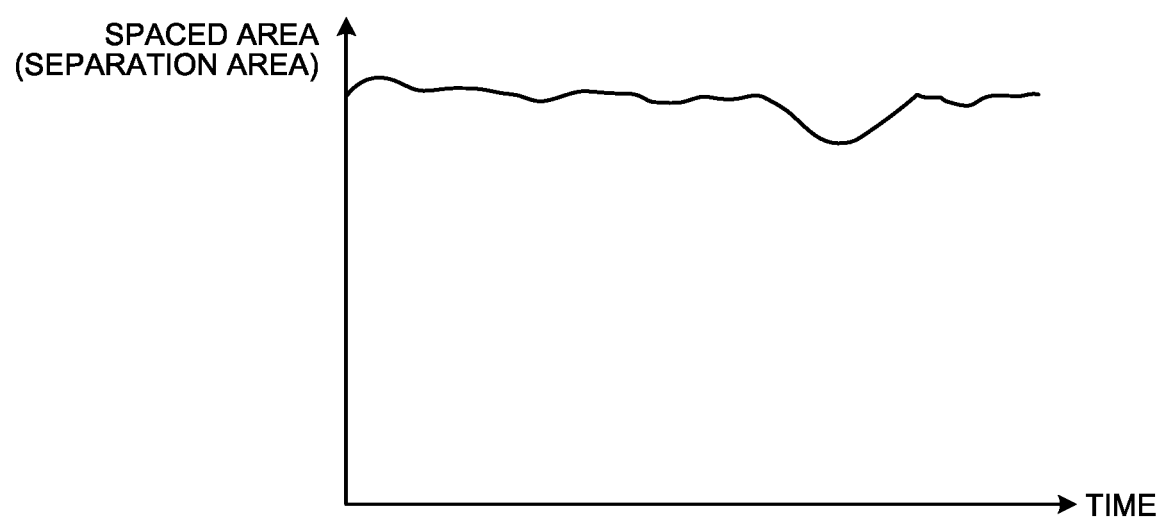
FIG. 20 is a diagram for explaining an example of a process performed by the fifth modification example.

So far, the case where the measurement function 354 measures a separation area in one time phase by using the three-dimensional CT image data of one time phase has been described. However, by using each piece of the three-dimensional CT image data of the time phases constituting the four-dimensional CT image data, the measurement function 354 may also measure a separation area in each of the time phases. FIG. 20 is a diagram for explaining an example of a process performed by the fifth modification example. In such a case, as illustrated in FIG. 20, the generation function 355 generates image data indicating a graph, in which a horizontal axis is set as time (time phase) and a vertical axis is set as a spaced area (separation area) and which represents a separation area for each time phase, by using the separation areas in the time phases measured by the measurement function 354.

Then, the control function 351 transmits the image data generated by the generation function 355 to the display 340 and controls the display 340 to display the graph indicated by the image data.

The measurement function 354 may also measure an area of "a part of the aforementioned valve leaflet 40b" forming the separation region 42 as a separation area in the same manner.

Sixth Modification Example of First Embodiment

Figure 21:
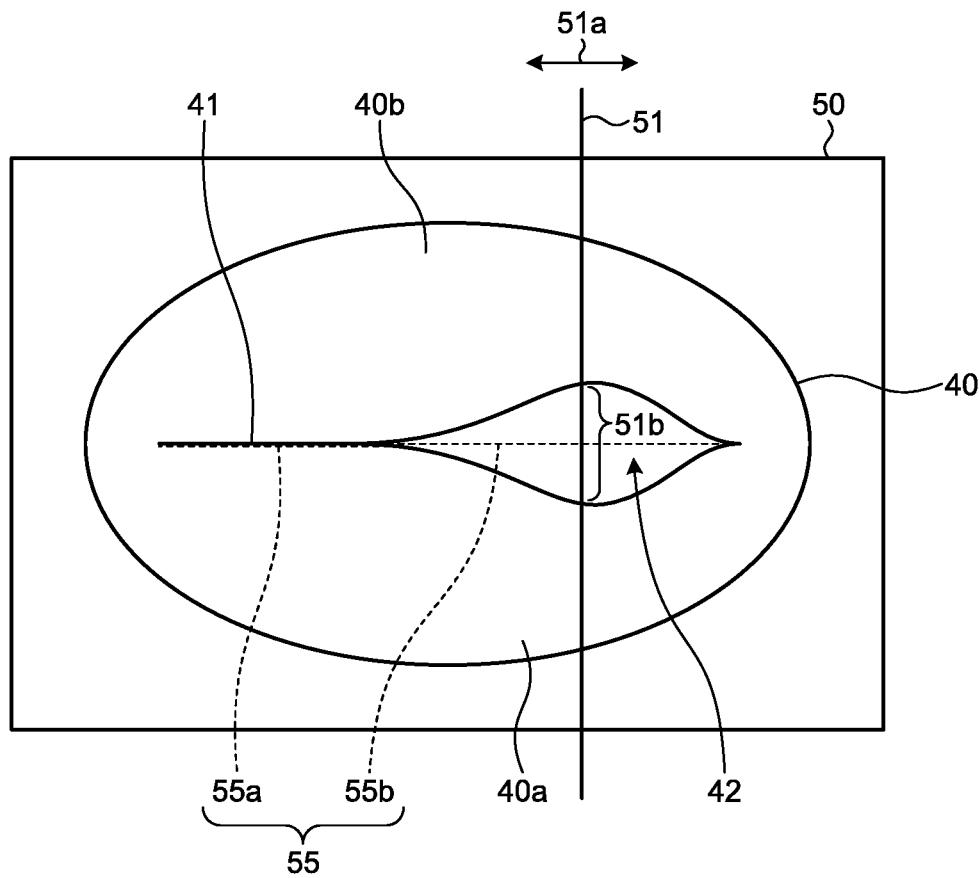
FIG. 21 is a diagram for explaining an example of a process performed by a sixth modification example.

Next, the sixth modification example of measuring information indicating the detailed condition of a fifth valve will be described. FIG. 21 is a diagram for explaining an example of a process performed by the sixth modification example. As illustrated in FIG. 21, the measurement function 354 measures a distance 51b between the valve leaflet 40a and the valve leaflet 40b in the separation region 42. A specific example will be described. The measurement function 354 measures the distance 51b between the valve leaflet 40a and the valve leaflet 40b on the reference surface 50 and in the separation region 42 on the reference surface 51. The distance 51b is also referred to as a gap width. For example, the measurement function 354 may also measure a plurality of distances 51b at a plurality of positions on the reference surface 51 while moving the reference surface 51 along the boundary line 55b, and employ the longest one of the distances 51b as a distance between the valve leaflet 40a and the valve leaflet 40b in the separation region 42.

It is sufficient if, for at least one of the valve leaflets extracted by the extraction function 352, the measurement function 354 measures a distance between the at least one valve leaflet and another valve leaflet separated from each other in a separation region between the at least one valve leaflet and another valve leaflet.

Then, the control function 351 controls the display 340 to display the distance 51b measured by the measurement function 354.

Figure 22:
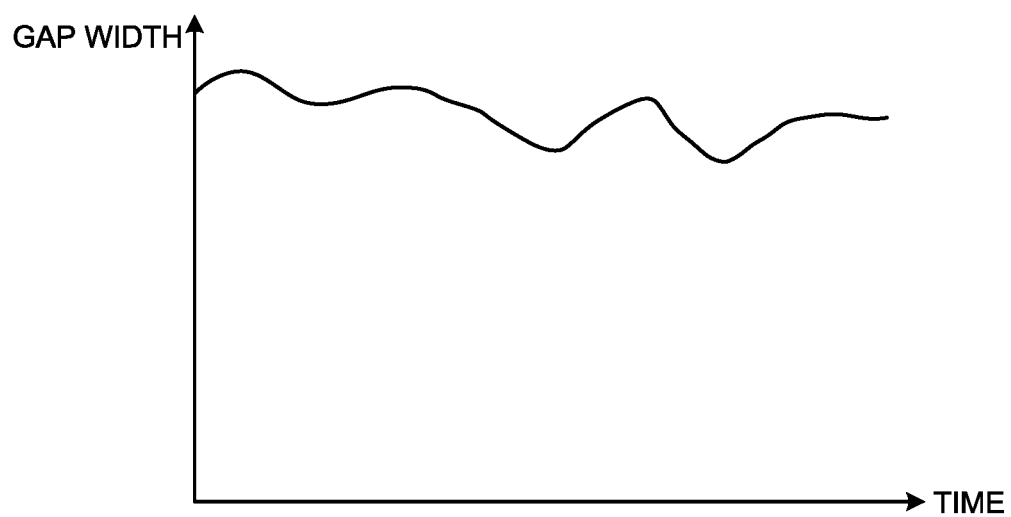
FIG. 22 is a diagram for explaining an example of a process performed by the sixth modification example.

So far, the case where the measurement function 354 measures the distance 51b in one time phase by using the three-dimensional CT image data of one time phase has been described. However, by using each piece of the three-dimensional CT image data of the time phases constituting the four-dimensional CT image data, the measurement function 354 may also measure the distances 51b in each of the time phases. FIG. 22 is a diagram for explaining an example of a process performed by the sixth modification example. In such a case, as illustrated in FIG. 22, the generation function 355 generates image data indicating a graph, in which a horizontal axis is set as time (time phase) and a vertical axis is set as a gap width (distances 51b) and which represents the distances 51b for each time phase, by using the distances 51b in the time phases measured by the measurement function 354.

Then, the control function 351 transmits the image data generated by the generation function 355 to the display 340 and controls the display 340 to display the graph indicated by the image data.

The control function 351 may also control the display 340 to display various measurement results measured by the measurement function 354 by using an indicator bar. In this way, it is possible to allow the user to quantitatively understand the length of a measured contact region in a direction along a boundary line.

Seventh Modification Example of First Embodiment

The aforementioned first embodiment and first to sixth modification examples have described the cases where, in the 2-leaflet valve such as the mitral valve 40, the setting function 353 sets the reference surface 51 orthogonal to the reference surface 50 and orthogonal to the line segment that connects the two commissures of the 2-leaflet valve. However, the setting function 353 may also set the reference surface 51 by other methods. Therefore, such a modification example will be described as a seventh modification example of the first embodiment.

Figure 23:
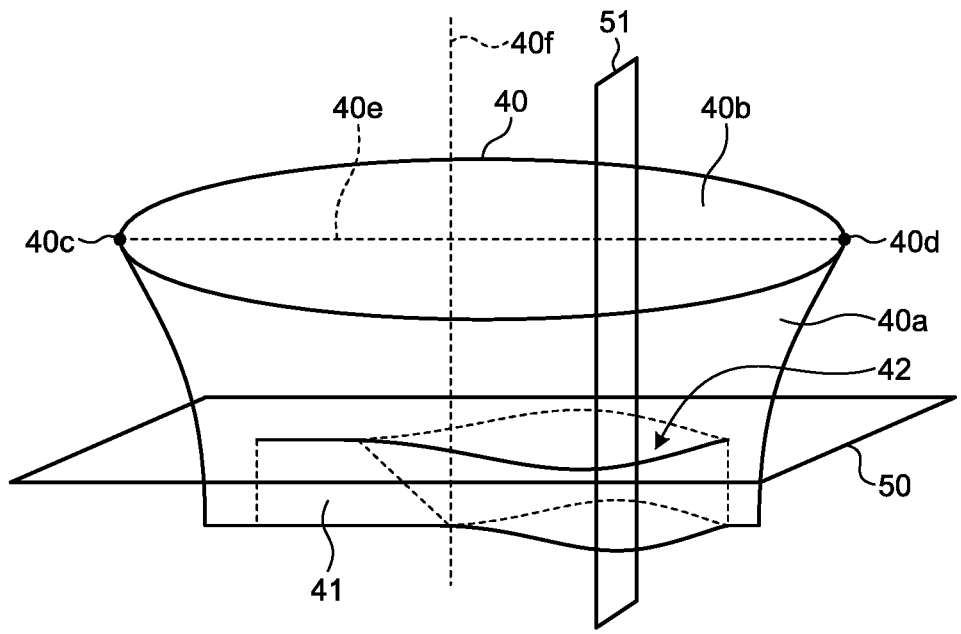
FIG. 23 is a diagram for explaining an example of a process performed by the setting function according to a seventh modification example of the first embodiment.

FIG. 23 is a diagram for explaining an example of a process performed by the setting function according to the seventh modification example of the first embodiment. The seventh modification example will be described while focusing on the differences from the aforementioned first embodiment and first to sixth modification examples. Furthermore, in the description of the seventh modification example, the same components as those of the aforementioned first embodiment and first to sixth modification examples are denoted by the same reference numerals and a description thereof will be omitted.

In the seventh modification example, for example, as illustrated in FIG. 23, the setting function 353 detects a long axis 40f of the heart included in the CT image data. The long axis 40f is an axis that connects the apex of the heart and the tip of the mitral valve 40. Then, the setting function 353 sets the reference surface 51, which is orthogonal to the line segment 40e, along the long axis 40f. The setting function 353 may also set the reference surface 51, which is orthogonal to the reference surface 50, along the long axis 40f.

Furthermore, for example, a case in which the setting function 353 sets the reference surface 51 with respect to the aortic valve composed of three valve leaflets will be described as an example. In such a case, the setting function 353 extracts a core line (not illustrated) of the aorta. The aorta is a blood vessel that carries blood having flowed in through the aortic valve. Then, the setting function 353 sets the reference surface 51, which is orthogonal to a line segment connecting the aforementioned contact point or center of gravity and the commissure, along the core line. The setting function 353 may also set the reference surface 51, which is orthogonal to the reference surface 50, along the core line.

Furthermore, for example, a case in which the setting function 353 sets the reference surface 51 with respect to the pulmonary valve composed of three valve leaflets will be described as an example. In such a case, the setting function 353 extracts a core line (not illustrated) of the pulmonary artery. The pulmonary artery is a blood vessel that carries blood having flowed in through the pulmonary valve. Then, the setting function 353 sets the reference surface 51, which is orthogonal to a line segment connecting the aforementioned contact point or center of gravity and the commissure, along the core line. The setting function 353 may also set the reference surface 51, which is orthogonal to the reference surface 50, along the core line.

Eighth Modification Example of First Embodiment

The measurement function 354 may also measure the inclination angle of a valve leaflet and the length of the contact region in the inclination direction of the valve leaflet. Therefore, such a modification example will be described as an eighth modification example of the first embodiment.

Figure 24:
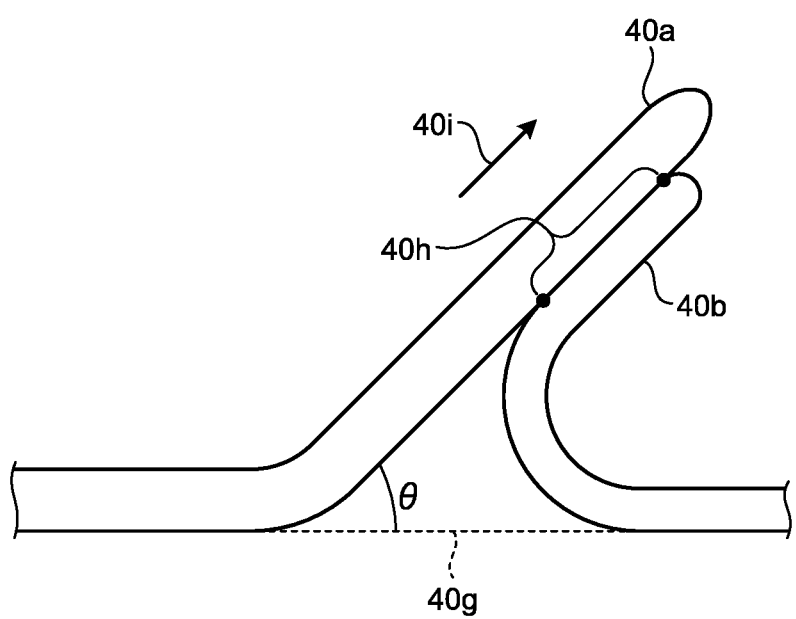
FIG. 24 is a diagram for explaining an example of a process performed by the setting function according to an eighth modification example of the first embodiment.

FIG. 24 is a diagram for explaining an example of a process performed by the setting function according to the eighth modification example of the first embodiment. The eighth modification example will be described while focusing on the differences from the aforementioned first embodiment and first to seventh modification examples. Furthermore, in the description of the eighth modification example, the same components as those of the aforementioned first embodiment and first to seventh modification examples are denoted by the same reference numerals and a description thereof will be omitted.

As illustrated in FIG. 24, the measurement function 354 derives an angle θ between a line segment 40g on the reference surface 51 and the valve leaflet 40a as the inclination angle of the valve leaflet 40a. The line segment 40g is a line segment parallel to the line segment 40e. The line segment 40g may be a line segment parallel to a line segment intersecting with the reference surface 50 and the reference surface 51.

Then, the measurement function 354 specifies a direction, in which the valve leaflet 40a extends (direction indicated by an arrow 40i, extension direction), from the inclination angle θ of the valve leaflet 40a. Then, the measurement function 354 measures the length of the contact region on the reference surface 51 in the extension direction. That is, the measurement function 354 measures the length of the contact region in the direction in which the valve leaflet 40a extends.

The measurement function 354 may also measure the length of the contact region, which intersects with the reference surface 51, on the reference surface 51 as the length of the contact region 41 in the extension direction.

Ninth Modification Example of First Embodiment

The control function 351 may also allow the display 340 to display other images, in addition to the display in the first embodiment and the first to eighth modification examples. Therefore, such a modification example will be described as a ninth modification example of the first embodiment.

With reference to FIG. 15, the ninth modification example will be described. For example, the generation function 355 according to the ninth modification example generates volume rendering image data of a predetermined range, which passes through the mark 87a on the boundary line 84a illustrated in FIG. 15 and includes the valve leaflet 83c and the valve leaflet 83a.

In such a case, the generation function 355 generates volume rendering image data in which a predetermined color is assigned to the contact region where the valve leaflet 83c and the valve leaflet 83a contact with each other. As the predetermined color, for example, a color is employed to allow the contact region to be conspicuous to a region around the contact region when the volume rendering image is displayed on the display 340. For example, the predetermined color is a red color.

As described above, the mark 87a is movable on the boundary line 84a by the user's manipulation via the input interface 330. For example, the generation function 355 moves the marks 87a to 87c to the positions designated by the user. Therefore, the generation function 355 generates new volume rendering image data depending on the position of the moved mark 87a.

That is, the generation function 355 receives the designation of the position on the boundary line 84a, and generates volume rendering image data in which the designated position is included and the two adjacent valve leaflets 83c and 83a are drawn and in which a predetermined color is assigned to the contact region where the two valve leaflets 83c and 83a contact with each other.

Then, the control function 351 allows the display 340 to display a volume rendering image indicated by the volume rendering image data. In this way, in the volume rendering image three-dimensionally viewed by the user, the contact region is three-dimensionally displayed. Furthermore, since a conspicuous color is assigned to the contact region, the user can easily understand the shape and position of the contact region.

Consequently, according to the ninth modification example, it is possible to allow the user to easily understand the shape and position of the contact region.

Second Embodiment

Figure 25:
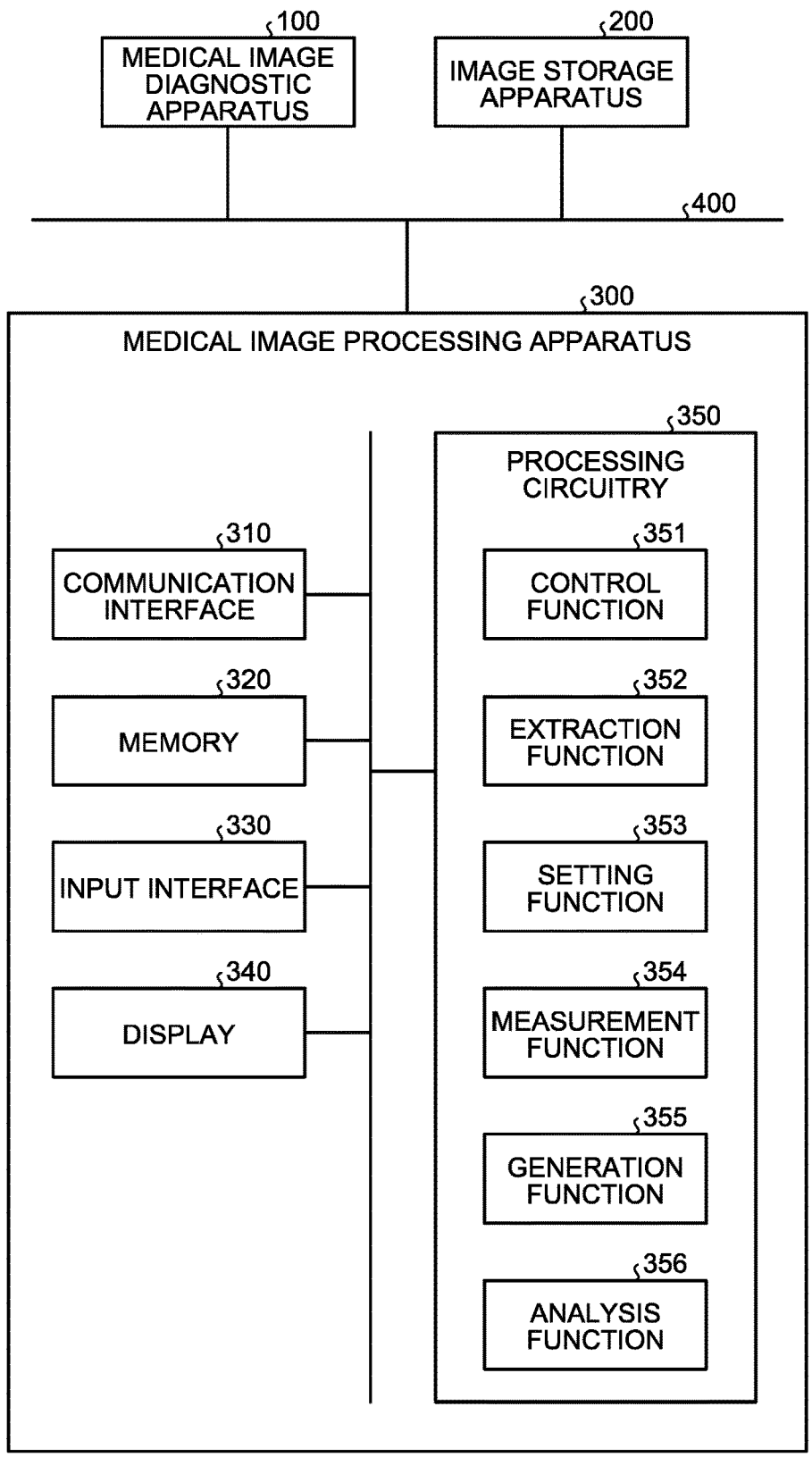
FIG. 25 is a diagram illustrating an example of a configuration of a medical image processing apparatus according to a second embodiment.

Next, a medical image processing apparatus 300 according to a second embodiment will be described. FIG. 25 is a diagram illustrating an example of a configuration of the medical image processing apparatus 300 according to the second embodiment. The medical image processing apparatus 300 according to the second embodiment is different from the medical image processing apparatus 300 according to the first embodiment in that the processing circuitry 350 further has an analysis function 356. In the description of the second embodiment, the same components as those of the first embodiment are denoted by the same reference numerals and a description thereof will be omitted.

The analysis function 356 according to the second embodiment performs various simulations by using the measurement result of the measurement function 354. For example, on the basis of the measurement result of the measurement function 354, the analysis function 356 performs a simulation on the valve composed of the valve leaflets extracted by the extraction function 352, thereby obtaining the amount of backflow of blood when the blood flowing through the valve flows backward.

For example, by using the time for which two valve leaflets constituting the mitral valve are opened during normal systole in which the mitral valve is completely closed, the length of the separation region measured by the measurement function 354 in a direction along the boundary line during the systole, the contraction rate of the left ventricle of the heart of the subject, and the heartbeat ejection amount of the heart of the subject, the analysis function 356 performs a fluid simulation for obtaining the amount of backflow, backflow position, or the like of blood when the blood flowing through the mitral valve flows backward.

The time for which the two valve leaflets constituting the mitral valve are opened during the systole is obtained by the medical image processing apparatus 300 from four-dimensional CT image data including three-dimensional CT image data of the time phase of the systole. For example, the medical image processing apparatus 300 can calculate the time for which the two valve leaflets are opened by measuring the length of the contact region in the blood flow direction in each time phase of the systole.

Furthermore, the heartbeat ejection amount of the heart of the subject is also obtained by the medical image processing apparatus 300 using the four-dimensional CT image data by the well-known technology. Furthermore, the contraction rate of the left ventricle of the heart of the subject is also obtained by the medical image processing apparatus 300 using the four-dimensional CT image data by the well-known technology.

When performing the aforementioned fluid simulation, the analysis function 356 may also perform the fluid simulation by using the length of the separation region in the direction along the boundary line in a valve after a valve forming operation assumed by a doctor, instead of the length of the separation region measured by the measurement function 354 in the direction along the boundary line. In this way, a simulation after the operation of the valve is performed, so that the user can obtain a valve forming method suitable for the operation.

Furthermore, the analysis function 356 may also superimpose information indicating the amount of backflow of blood obtained by the fluid simulation on a position where a valve leaflet and a valve leaflet are separated from each other on an MPR image. The MPR image described herein, for example, includes the MPR image 76 illustrated in FIG. 13, the MPR images 80 and 81a to 81c illustrated in FIG. 15, or the like.

Furthermore, when performing the aforementioned fluid simulation, the analysis function 356 may also perform the fluid simulation by using information on the valve leaflets and the valve annulus of a plurality of biological and mechanical valves that are candidates to be replaced with the valve of the subject in a valve replacement operation, instead of the length of the separation region measured by the measurement function 354 in the direction along the boundary line. In this way, the user can determine a biological valve and a mechanical valve optimal for preventing backflow among the candidates.

Third Embodiment

In the aforementioned embodiment, the case where the medical image processing apparatus 300 performs various processes has been described. However, the embodiments are not limited thereto, and for example, a medical image diagnostic apparatus may also perform various processes. Hereinafter, a case where the medical image diagnostic apparatus for performing various processes is an X-ray CT apparatus will be described; however, the medical image diagnostic apparatus for performing various processes may be an ultrasonic diagnostic apparatus, a magnetic resonance imaging apparatus, or an X-ray diagnostic apparatus. FIG. 26 is a diagram illustrating an example of a configuration of an X-ray CT apparatus according to a third embodiment.

For example, as illustrated in FIG. 26, an X-ray CT apparatus 500 according to the third embodiment has a gantry 10, a couch 20, and a console 30.

The gantry 10 is a device that radiates a subject P with X-rays and collects data related to the X-rays transmitted through the subject P, and has an X-ray high-voltage device 11, an X-ray generator 12, an X-ray detector 13, data acquisition circuitry 14, a rotating frame 15, and a gantry control device 16. As illustrated in FIG. 26, in the gantry 10, an orthogonal coordinate system with an X axis, a Y axis, and a Z axis is defined. That is, the X axis indicates a horizontal direction, the Y axis indicates a vertical direction, and the Z axis indicates an axial direction of the rotation center of the rotating frame 15 when the gantry 10 is in a non-tilted state.

The rotating frame 15 is an annular frame that supports the X-ray generator 12 and the X-ray detector 13 so as to face each other with the subject P interposed therebetween, and is rotated by the gantry control device 16, which will be described below, at a high speed in a circular orbit centered as the subject P.

The X-ray generator 12 is a device that generates the X-rays and radiates the generated X-rays to the subject P. The X-ray generator 12 has an X-ray tube 12a, a wedge 12b, and a collimator 12c.

The X-ray tube 12a is a vacuum tube that receives the supply of a high voltage from the X-ray high-voltage device 11 and emits thermoelectrons toward an anode (target) from a cathode (also referred to as filament), and radiates X-ray beams to the subject P along with the rotation of the rotating frame 15. That is, the X-ray tube 12a generates the X-rays by using the high voltage supplied from the X-ray high-voltage device 11.

Furthermore, the X-ray tube 12a generates X-ray beams that spread with a fan angle and a cone angle. For example, under the control of the X-ray high-voltage device 11, the X-ray tube 12a can continuously emit the X-rays in the entire surrounding of the subject P in order to achieve full reconstruction or continuously emit the X-rays to an emission range (180°+fan angle), which enables half reconstruction, in order to achieve the half reconstruction. Furthermore, under the control of the X-ray high-voltage device 11, the X-ray tube 12a can intermittently emit the X-rays (pulse X-rays) at positions (X-ray tube positions) set in advance. Furthermore, the X-ray high-voltage device 11 can also modulate the intensities of the X-rays emitted from the X-ray tube 12a. For example, the X-ray high-voltage device 11 increases the intensities of the X-rays emitted from the X-ray tube 12a at a specific X-ray tube position, and decreases the intensities of the X-rays emitted from the X-ray tube 12a in a range other than the specific X-ray tube position.

The wedge 12b is an X-ray filter for adjusting the X-ray dose of the X-rays emitted from the X-ray tube 12a. Specifically, the wedge 12b is a filter that transmits and attenuates the X-rays emitted from the X-ray tube 12a such that the X-rays radiated to the subject P from the X-ray tube 12a have a predetermined distribution. For example, the wedge 12b is a filter obtained by processing aluminum to have a predetermined target angle and a predetermined thickness. The wedge is also referred to as a wedge filter or a bow-tie filter.

The collimator 12c is configured with a lead plate or the like, and has a slit at a part thereof. For example, the collimator 12c narrows down the radiation range of the X-rays, of which X-ray dose has been adjusted by the wedge 12b, with the user of the slit under the control of the X-ray high-voltage device 11 to be described below.

An X-ray source of the X-ray generator 12 is not limited to the X-ray tube 12a. For example, the X-ray generator 12 may also be configured with a focus coil for converging electron beams generated from an electron gun, a deflection coil for electromagnetically deflecting the electron beams, and a target ring for covering the semi-circumference of the subject P and generating the X-rays by collision with the deflected electron beams.

The X-ray high-voltage device 11 is composed of electric circuitry including a transformer, a rectifier, or the like, and is composed of a high-voltage generation device having a function of generating a high voltage to be applied to the X-ray tube 12a and an X-ray control device that controls an output voltage corresponding to the X-rays radiated by the X-ray tube 12a. The high-voltage generation device may be of a transformer type or an inverter type. For example, the X-ray high-voltage device 11 adjusts the X-ray dose radiated to the subject P by adjusting an X-ray tube voltage or an X-ray tube current to be supplied to the X-ray tube 12a. Furthermore, the X-ray high-voltage device 11 is controlled by processing circuitry 37 of the console 30.

The gantry control device 16 is composed of processing circuitry configured with a central processing unit (CPU) or the like and a driving mechanism such as a motor and an actuator. The gantry control device 16 has a function of controlling the operation of the gantry 10 by receiving an input signal from an input interface 31 attached to the console 30 or an input interface attached to the gantry 10. For example, the gantry control device 16 rotates the rotating frame 15 upon receiving the input signal, thereby performing control for revolving the X-ray tube 12a and the X-ray detector 13 in the circular orbit centered at the subject P, control for tilting the gantry 10, and control for operating the couch 20 and a couchtop 22. The gantry control device 16 is controlled by the processing circuitry 37 of the console 30.

Furthermore, the gantry control device 16 monitors the position of the X-ray tube 12a, and outputs a view trigger signal indicating a timing to start data acquisition to the data acquisition circuitry 14 when the X-ray tube 12a reaches a predetermined rotation angle (imaging angle). For example, when the total number of views in rotational imaging is 2,460 views, the gantry control device 16 outputs a view trigger signal whenever the X-ray tube 12a is moved by about 0.15° (=360/2,460) in the circular orbit.

The X-ray detector 13, for example, is composed of a plurality of arrays of X-ray detector elements (also referred to as "sensors" or simply "detector elements"), wherein each of the arrays includes a plurality of X-ray detector elements arranged in a channel direction along one arc centered at a focal point of the X-ray tube 12a. The X-ray detector 13 has a structure in which the plurality of arrays of X-ray detector elements are arranged in a slice direction, wherein each of the arrays of X-ray detector elements includes the plurality of X-ray detector elements arranged in the channel direction. Each X-ray detector element of the X-ray detector 13 detects the X-rays that have been emitted from the X-ray generator 12 and have passed through the subject P and outputs an electric signal (pulse) corresponding to the X-ray dose to the data acquisition circuitry 14.

Furthermore, the X-ray detector 13 is an indirect conversion-type detector composed of a grid, a scintillator array, and a photo sensor array. The scintillator array is composed of a plurality of scintillators, each of which is configured with a scintillator crystal that outputs light with a photon quantity corresponding to an incident X-ray dose. The grid is arranged on the surface of the scintillator array on an X-ray incident side and is configured with an X-ray blocking plate having a function of absorbing scatted X-rays. The photo sensor array has a function of converting light into electrical signals corresponding to the amount of light output from the scintillator, and for example, is composed of photo sensors such as photomultipliers. The photo sensors, for example, are silicon photomultipliers (SiPMs).

The X-ray detector 13 may also be a direct conversion-type detector composed of semiconductor elements that convert incident X-rays into electrical signals.

The data acquisition circuitry 14 (data acquisition system (DAS)) is composed of at least an amplifier that performs an amplification process on the electrical signals output from each X-ray detector element of the X-ray detector 13 and an analog-to-digital (A/D) converter that converts the electrical signals to digital signals, and generates detection data using the detection signals of the X-ray detector 13.

The couch 20 is a device for placing and moving the subject P to be scanned and includes a couch driving device 21, the couchtop 22, a pedestal 23, and a base (support frame) 24.

The couchtop 22 is a board on which the subject P is placed. The base 24 supports the couchtop 22. The pedestal 23 is a casing that supports the base 24 so as to be movable in the vertical direction. The couch driving device 21 is a motor or an actuator that moves the couchtop 22, on which the subject P is placed, in the longitudinal direction of the couchtop 22 so as to move the subject P into the rotating frame 15. The couch driving device 21 can also move the couchtop 22 in the X-axis direction.

As for the method of moving the couchtop, only the couchtop 22 may be moved, or the couch 20 may be moved together with the base 24. Furthermore, in a case of upright CT, it may be possible to move a subject moving mechanism corresponding to the couchtop 22.

The gantry 10, for example, performs helical scan for helically scanning the subject P by rotating the rotating frame 15 while moving the couchtop 22. Alternatively, the gantry 10 performs conventional scan for scanning the subject P in a circular orbit by rotating the rotating frame 15 after moving the couchtop 22 and fixing the position of the subject P. In the following embodiment, an example in which the relative position between the gantry 10 and the couchtop 22 is changed by controlling the couchtop 22 will be described; however, possible embodiments are not limited to this embodiment. For example, when the gantry 10 is self-propelled, the relative position between the gantry 10 and the couchtop 22 may be changed by controlling the self-propelled movement of the gantry 10. Furthermore, the relative position between the gantry 10 and the couchtop 22 may be changed by controlling the self-propelled movement of the gantry 10 and the couchtop 22.

The console 30 is a device that receives manipulation performed by an operator on the medical image diagnostic apparatus 100 and reconstructs CT image data by using projection data collected by the gantry 10. As illustrated in FIG. 26, the console 30 includes the input interface 31, a display 32, a memory 35, and the processing circuitry 37.

The input interface 31 receives various kinds of input manipulation from the operator, converts the received input manipulation into an electrical signal, and outputs the electrical signal to the processing circuitry 37. For example, the input interface 31 receives, from the operator, a collection condition used when projection data is collected, a reconstruction condition used when CT image data is reconstructed, an image processing condition used when a post-processing image is generated from the CT image data, or the like. For example, the input interface 31 is implemented by a mouse, a keyboard, a trackball, a switch, a button, a joystick, or the like.

The display 32 displays various kinds of information. For example, the display 32 outputs a medical image (CT image) generated by the processing circuitry 37, a GUI for receiving various kinds of manipulation from the operator, or the like. For example, the display 32 is configured with a liquid crystal display, a CRT display, or the like.

The memory 35, for example, is implemented by a semiconductor memory element such as a RAM and a flash memory, a hard disk, an optical disc, or the like. The memory 35, for example, stores therein the projection data or the CT image data.

The processing circuitry 37, for example, performs a control function 37a, an extraction function 37b, a setting function 37c, a measurement function 37d, and a generation function 37e. For example, processing functions performed by the components of the processing circuitry 37 illustrated in FIG. 26, that is, the processing functions performed by the control function 37a, the extraction function 37b, the setting function 37c, the measurement function 37d, and the generation function 37e are stored in the memory 35 in the form of computer programs executable by a computer. The processing circuitry 37 is a processor, for example, and reads the computer programs from the memory 35 and execute the read computer programs to thereby implement functions corresponding to the computer programs. In other words, the processing circuitry 37 having read the computer programs has the functions that are included in the processing circuitry 37 in FIG. 26.

The control function 37a controls the entire medical image diagnostic apparatus 100. Furthermore, the control function 37a performs the same process as the aforementioned control function 351. The extraction function 37b performs the same process as the aforementioned extraction function 352. The setting function 37c performs the same process as the aforementioned setting function 353. The measurement function 37d performs the same process as the aforementioned measurement function 354. The generation function 37e performs the same process as the aforementioned generation function 355.

Furthermore, the generation function 37e generates three-dimensional CT image data on the basis of the collected projection data. For example, the generation function 37e collects projection data obtained by imaging a region including the valve of the heart of the subject P, and generates three-dimensional CT image data on the basis of the acquired projection data. The generation function 37e can also acquire the projection data obtained by imaging the region including the valve of the heart of the subject P, and generate four-dimensional CT image data on the basis of the collected projection data. By so doing, the generation function 37e collects the three-dimensional CT image data and the four-dimensional CT image data. The generation function 37e is an example of a generation unit and a collection unit.

Furthermore, in the aforementioned embodiments, the cases where various processing functions are implemented by the single processing circuitry (the processing circuitry 350 or the processing circuitry 37) have been described; however, possible embodiments are not limited to the embodiments. For example, the processing circuitry 350 and the processing circuitry 37 may be configured by combining a plurality of independent processors, and each processing function may be implemented by each processor that executes each computer program. Furthermore, the processing functions of the processing circuitry 350 and the processing circuitry 37 may be implemented by being appropriately distributed or integrated into a single or a plurality of processing circuitries.

The term "processor" used in the description of the aforementioned each embodiment, for example, means a circuitry of a central processing unit (CPU), a graphics processing unit (GPU), an application specific integrated circuit (ASIC), a programmable logic device (for example, a simple programmable logic device (SPLD), a complex programmable logic device (CPLD), and a field programmable gate array (FPGA)), or the like. Instead of storing the computer program in the memory, the computer program may also be directly incorporated in the circuitry of the processor. In such a case, the processor implements the functions by reading and executing the computer program incorporated in the circuitry. Furthermore, each processor of the present embodiment is not limited to a case where a single circuitry is configured for each processor, and one processor may be configured by combining a plurality of independent circuitries to implement the functions thereof.

The computer program executed by the processor is provided after being incorporated in advance in a read only memory (ROM), a storage unit, or the like. The computer program may be provided after being recorded in a computer readable storage medium such as a compact disc-ROM (CD-ROM), a flexible disk (FD), a CD-R (recordable), and a digital versatile disc (DVD) in the form of a file having a format installable or executable in these devices. Furthermore, the computer program may be provided or distributed after being stored on a computer connected to a network such as the Internet and downloaded via the network. For example, the computer program is configured with a module including each functional unit. As actual hardware, the CPU reads and executes the computer program from the storage medium such as the ROM, so that each module is loaded on a main storage device and is generated on the main storage device.

According to the aforementioned at least one embodiment, it is possible to allow the user to understand the detailed condition of the valve.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical image processing apparatus comprising:
processing circuitry configured to
extract a plurality of valve leaflets of a heart valve from image data of a subject,
measure, with respect to at least one valve leaflet of the valve leaflets, a length of a region at which the valve leaflet is in contact with another valve leaflet, in a predetermined reference direction, and
control a display to display a distribution of the length at each of a plurality of positions on the valve leaflet.

2. The medical image processing apparatus according to claim 1, wherein the processing circuitry sets, with respect to the at least one valve leaflet, a reference surface related to the valve leaflet,
controls the display to display an image which is a first tomographic image superimposed with a line segment, the first tomographic image being a tomographic image at a position approximately corresponding to the reference surface in the image data, and the line segment corresponding to a region at which two valve leaflets contact with each other in the first tomographic image, and
controls the display to display the distribution of the length at each of a plurality of positions on the line segment.

3. The medical image processing apparatus according to claim 2, wherein the processing circuitry measures, as the length in the predetermined reference direction, a length of the region in a direction, which is approximately perpendicular to the reference surface.

4. The medical image processing apparatus according to claim 2, wherein the processing circuitry extracts two valve leaflets constituting the heart valve, and
measures a length of the region on a surface which is orthogonal to the reference surface and is orthogonal to a line segment that connects two commissures of the heart valve.

5. The medical image processing apparatus according to claim 2, wherein the processing circuitry extracts two valve leaflets constituting the heart valve, and measures a length of the region on a surface which is orthogonal to the reference surface and is along a long axis of a heart.

6. The medical image processing apparatus according to claim 2, wherein the processing circuitry extracts two valve leaflets constituting the heart valve, and
measures a length of the region on a surface which is orthogonal to a line segment that connects two commissures of the heart valve and is along a long axis of a heart.

7. The medical image processing apparatus according to claim 2, wherein the processing circuitry extracts three valve leaflets constituting the heart valve, and
measures a length of the region on a surface which is orthogonal to the reference surface and is orthogonal to a line segment that connects a commissure of the heart valve and a point at which the three valve leaflets intersect with one another, or center of gravity of a region surrounded by the three valve leaflets.

8. The medical image processing apparatus according to claim 2, wherein the processing circuitry extracts three valve leaflets constituting the heart valve, and
measures a length of the region on a surface which is orthogonal to the reference surface and is along a core line of a blood vessel that carries blood having flowed in through the heart valve.

9. The medical image processing apparatus according to claim 2, wherein the processing circuitry extracts three valve leaflets constituting the heart valve, and
measures a length of the region on a surface which is orthogonal to a line segment and is along a core line of a blood vessel that carries blood having flowed in through the heart valve, the line segment connecting a commissure of the heart valve and a point at which the three valve leaflets intersect with one another, or center of gravity of a region surrounded by the three valve leaflets.

10. The medical image processing apparatus according to claim 2, wherein, the processing circuitry measures, with respect to the at least one valve leaflet, the length in a direction intersecting with the line segment and a direction intersecting with the reference surface.

11. The medical image processing apparatus according to claim 2, wherein the processing circuitry generates first tomographic image data including the valve leaflets from the image data, and
controls the display to display the first tomographic image indicated by the first tomographic image data, together with the distribution.

12. The medical image processing apparatus according to claim 11, wherein the processing circuitry superimposes the line segment, which has different modes at a portion where the length is equal to or more than a threshold value, and a portion where the length is smaller than the threshold value, on the first tomographic image, and
controls the display to display the first tomographic image superimposed with the line segment.

13. The medical image processing apparatus according to claim 12, wherein the line segment indicates a boundary between two adjacent valve leaflets, and
the processing circuitry receives designation of a position on the line segment, and generates second tomographic image data in which the designated position is included and the two adjacent valve leaflets are drawn, and controls the display to display a second tomographic image indicated by the second tomographic image data.

14. The medical image processing apparatus according to claim 12, wherein the line segment indicates a boundary between two adjacent valve leaflets, and
the processing circuitry receives designation of a position on the line segment, and generates volume rendering image data in which the designated position is included and the two adjacent valve leaflets are drawn and in which a predetermined color is assigned to a contact region at which the two valve leaflets contact with each other, and controls the display to display a volume rendering image indicated by the volume rendering image data.

15. The medical image processing apparatus according to claim 1, wherein the processing circuitry measures, as the length in the predetermined reference direction, a length of the region in a blood flow direction.

16. The medical image processing apparatus according to claim 1, wherein the processing circuitry measures, as the length in the predetermined reference direction, a length of the region in a direction, in which the valve leaflet extends.

17. The medical image processing apparatus according to claim 1, wherein the processing circuitry measures the length of the region at each of the positions in a direction intersecting with the predetermined reference direction, and
controls the display to display the distribution of the length at the positions.

18. The medical image processing apparatus according to claim 1, wherein the processing circuitry measures, with respect to the at least one valve leaflet, a length of the region at which the valve leaflet and the another valve leaflet contact with each other, in a direction intersecting with the predetermined reference direction, and
controls the display to display the length of the region in the direction intersecting with the predetermined reference direction.

19. The medical image processing apparatus according to claim 1, wherein the processing circuitry measures, with respect to the at least one valve leaflet, a length of a separation region between the valve leaflet and the another valve leaflet separated from each other, in a direction intersecting with the predetermined reference direction, and
controls the display to display the length of the separation region in the direction intersecting with the predetermined reference direction.

20. The medical image processing apparatus according to claim 19, wherein, based on the measured length of the separation region in the direction intersecting with the predetermined reference direction, the processing circuitry performs a simulation for obtaining an amount of backflow of blood when the blood flowing through the heart valve flows backward in the heart valve.

21. The medical image processing apparatus according to claim 1, wherein the processing circuitry measures, with respect to the at least one valve leaflet, a contact area of the region at which the valve leaflet and the another valve leaflet contact with each other, and
controls the display to display the contact area.

22. The medical image processing apparatus according to claim 1, wherein the processing circuitry measures, with respect to the at least one valve leaflet, a separation area in a separation region between the valve leaflet and the another valve leaflet separated from each other, and
controls the display to display the separation area.

23. The medical image processing apparatus according to claim 1, wherein the processing circuitry measures, with respect to the at least one valve leaflet, a distance between the valve leaflet and the another valve leaflet separated from each other in a separation region between the valve leaflet and the another valve, and controls the display to display the distance.

24. A medical image processing apparatus comprising: processing circuitry configured to extract a plurality of valve leaflets of a heart valve from image data of a subject, measure, with respect to at least one valve leaflet of the valve leaflets, an index indicating a degree of close contact in a region at which the valve leaflet is in contact with another valve leaflet, and control a display to display the index at each of a plurality of positions on the valve leaflet.

25. A medical image diagnostic apparatus comprising: processing circuitry configured to collect image data of a subject, extract a plurality of valve leaflets of a heart valve from the image data, measure, with respect to at least one valve leaflet of the valve leaflets, a length of a region at which the valve leaflet is in contact with another valve leaflet, in a predetermined reference direction, and control a display to display a distribution of the length at each of a plurality of positions on the valve leaflet.

26. A computer readable non-transitory storage medium stored with a medical image processing program comprising instructions that cause a computer to execute:

extracting a plurality of valve leaflets of a heart valve from image data of a subject, measuring, with respect to at least one valve leaflet of the valve leaflets, a length of a region at which the valve leaflet is in contact with another valve leaflet, in a predetermined reference direction, and controlling a display to display a distribution of the length at each of a plurality of positions on the valve leaflet.

* * * * *